US012661422B2

(12) United States Patent
Hebrink et al.

(10) Patent No.: US 12,661,422 B2
(45) Date of Patent: Jun. 23, 2026

(54) MULTILAYER ARTICLES INCLUDING AN ABSORBENT LAYER AND AN ULTRAVIOLET MIRROR, SYSTEMS, DEVICES, AND METHODS OF DISINFECTING

(71) Applicant: 3M INNOVATIVE PROPERTIES COMPANY, St. Paul, MN (US)

(72) Inventors: Timothy J. Hebrink, Scandia, MN (US); John A. Wheatley, Stillwater, MN (US); Bharat R. Acharya, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 447 days.

(21) Appl. No.: 18/246,241

(22) PCT Filed: Oct. 12, 2021

(86) PCT No.: PCT/IB2021/059349
§ 371 (c)(1),
(2) Date: Mar. 22, 2023

(87) PCT Pub. No.: WO2022/079597
PCT Pub. Date: Apr. 21, 2022

(65) Prior Publication Data
US 2023/0355821 A1    Nov. 9, 2023

Related U.S. Application Data

(60) Provisional application No. 63/252,207, filed on Oct. 5, 2021, provisional application No. 63/091,391, filed on Oct. 14, 2020.

(51) Int. Cl.
*A61L 2/26*        (2006.01)
*A61L 2/10*        (2026.01)
(Continued)

(52) U.S. Cl.
CPC .................. *A61L 2/26* (2013.01); *A61L 2/10* (2013.01); *B32B 27/08* (2013.01); *B32B 27/18* (2013.01);
(Continued)

(58) Field of Classification Search
None
See application file for complete search history.

(56) References Cited

U.S. PATENT DOCUMENTS 5,504,134 A     4/1996  Palmer et al.
5,876,688 A     3/1999  Laundon
(Continued)

FOREIGN PATENT DOCUMENTS

CN        109054586 A      12/2018
DE          4302555 A1      9/1993
(Continued)

OTHER PUBLICATIONS

International Search Report for PCT Application No. PCT/IB2021/059349, mailed on Dec. 14, 2021, 4 pages.
(Continued)

*Primary Examiner* — Shan Liu
(74) *Attorney, Agent, or Firm* — Adrian L. Pishko; Philip P. Soo

(57) ABSTRACT

Multilayer articles are provided, including an absorbent layer and an ultraviolet mirror containing at least a plurality of alternating first and second optical layers. The absorbent layer absorbs ultraviolet light having a wavelength between at least 230 nanometers (nm) and 400 nm. The ultraviolet mirror reflects ultraviolet light in a wavelength range from 190 nm to 240 nm. Systems are also provided including a broadband UVC light source and a multilayer article. Devices are provided including a chamber, a broadband UVC light source located within the chamber, an absorbent layer in the chamber, and an ultraviolet mirror between the
(Continued)

light source and absorbent layer. Methods of disinfecting a material are further provided, including obtaining a system or device, directing UVC light at the ultraviolet mirror, and exposing the material to ultraviolet light in a wavelength range from 190 nm to 240 nm, reflected by the ultraviolet mirror towards the material.

19 Claims, 5 Drawing Sheets

(51) Int. Cl.

| | |
|---|---|
| *B32B 27/08* | (2006.01) |
| *B32B 27/18* | (2006.01) |
| *B32B 27/30* | (2006.01) |
| *G02B 1/04* | (2006.01) |
| *G02B 5/08* | (2006.01) |
| *G02B 5/20* | (2006.01) |
| *H01J 61/02* | (2006.01) |

(52) U.S. Cl.

CPC .............. *B32B 27/304* (2013.01); *G02B 1/04* (2013.01); *G02B 5/0891* (2013.01); *G02B 5/208* (2013.01); *H01J 61/025* (2013.01); *A61L 2202/11* (2013.01); *B32B 2255/10* (2013.01); *B32B 2255/20* (2013.01); *B32B 2255/28* (2013.01); *B32B 2264/1022* (2020.08); *B32B 2551/00* (2013.01)

(56) References Cited

U.S. PATENT DOCUMENTS

| | | | |
|---|---|---|---|
| 5,882,774 | A | 3/1999 | Jonza et al. |
| 6,045,894 | A | 4/2000 | Jonza et al. |
| 6,368,699 | B1 | 4/2002 | Gilbert et al. |
| 6,418,257 | B1 | 7/2002 | Nath |
| 6,447,537 | B1 | 9/2002 | Hartman |
| 6,531,230 | B1 | 3/2003 | Weber et al. |
| 6,667,095 | B2 | 12/2003 | Wheatley et al. |
| 6,783,349 | B2 | 8/2004 | Neavin et al. |
| 7,271,951 | B2 | 9/2007 | Weber et al. |
| 7,511,281 | B2 | 3/2009 | Cooper |
| 7,632,568 | B2 | 12/2009 | Padiyath et al. |
| 7,652,736 | B2 | 1/2010 | Padiyath et al. |
| 7,683,344 | B2 | 3/2010 | Tribelsky et al. |
| 7,952,805 | B2 | 5/2011 | Mcgurran et al. |
| 8,203,124 | B2 | 6/2012 | Havens et al. |
| 8,557,378 | B2 | 10/2013 | Yamanaka et al. |
| 8,753,575 | B2 | 6/2014 | Neister |
| 9,364,573 | B2 | 6/2016 | Deshays et al. |
| 9,459,386 | B2 | 10/2016 | Hebrink et al. |
| 9,523,516 | B2 | 12/2016 | Hebrink et al. |
| 9,657,177 | B1 | 5/2017 | Pringle et al. |
| 9,700,642 | B2 | 7/2017 | Neister |
| 10,071,262 | B2 | 9/2018 | Randers et al. |
| 10,111,976 | B2 | 10/2018 | Deshays et al. |
| 10,376,379 | B2 | 8/2019 | Songer |
| 11,073,766 | B2 | 7/2021 | Nottbohm |
| 11,281,017 | B2 | 3/2022 | Taguchi |
| 2004/0145288 | A1 | 7/2004 | Ouderkirk et al. |
| 2009/0087629 | A1 | 4/2009 | Everaerts et al. |
| 2009/0089137 | A1 | 4/2009 | Minert et al. |
| 2010/0028564 | A1 | 2/2010 | Cheng et al. |
| 2010/0040842 | A1 | 2/2010 | Everaerts et al. |
| 2010/0044582 | A1 | 2/2010 | Cooper et al. |
| 2011/0126968 | A1 | 6/2011 | Determan et al. |
| 2012/0229893 | A1* | 9/2012 | Hebrink ................. G02B 5/283 359/359 |
| 2013/0260146 | A1* | 10/2013 | Wright ................... B05D 3/067 524/588 |
| 2015/0177432 | A1* | 6/2015 | Hebrink ................. G02B 5/208 359/359 |
| 2015/0250907 | A1 | 9/2015 | Bilenko et al. |
| 2017/0182194 | A1 | 6/2017 | Shin et al. |
| 2017/0290934 | A1 | 10/2017 | Dobrinksy et al. |
| 2019/0298871 | A1* | 10/2019 | Dobrinsky ................ A61L 2/10 |
| 2024/0261449 | A1* | 8/2024 | Hebrink ................... A61L 2/10 |

FOREIGN PATENT DOCUMENTS

| | | | | |
|---|---|---|---|---|
| DE | 102014105478 | B3 | 7/2015 | |
| EP | 521553 | B1 | 4/1996 | |
| JP | 2002372627 | | 12/2002 | |
| JP | 2018175506 | A | 11/2018 | |
| WO | 1995017303 | A1 | 6/1995 | |
| WO | 1999039224 | A1 | 8/1999 | |
| WO | 2008128073 | A2 | 10/2008 | |
| WO | 2010078064 | A2 | 7/2010 | |
| WO | 2012003417 | A1 | 1/2012 | |
| WO | 2014022049 | A1 | 2/2014 | |
| WO | 2016196904 | A1 | 12/2016 | |
| WO | 2017172546 | A1 | 10/2017 | |
| WO | 2017176083 | A1 | 10/2017 | |
| WO | 2019130198 | A1 | 7/2019 | |
| WO | WO-2020070589 | A1 * | 4/2020 | .............. B32B 7/02 |
| WO | 2020136557 | A1 | 7/2020 | |
| WO | 2021137125 | A1 | 7/2021 | |

OTHER PUBLICATIONS

Kitamura, "A Practical High-Power Excimer Lamp Excited by a Microwave Discharge", Applied Surface Science, 1994, vol. 79/80, pp. 507-513.

Kogelschatz, "Silent-Discharge Driven Excimer UV Sources and Their Applications", Applied Surface Science, 1992, vol. 54, pp. 410-423.

Parkyn, et al., "The Black hole™: Cuspated waveguide-injectors and illuminators for LEDs", Proc. SPIE 3781, Nonimaging Optics: Maximum Efficiency Light Transfer V, (Oct. 6, 1999), in section 5 ("Lighthouse" Equatorial Outputs from Hemispheric Sources).

Skakun, "Ultraviolet and Vacuum Ultraviolet Excimer Lamps Pumped by a Barrier Discharge", Technical Physics, Oct. 1994, vol. 39, No. 10, pp. 1054-1056.

* cited by examiner

MULTILAYER ARTICLES INCLUDING AN ABSORBENT LAYER AND AN ULTRAVIOLET MIRROR, SYSTEMS, DEVICES, AND METHODS OF DISINFECTING

FIELD

The present disclosure generally relates to the use of selected wavelengths of ultraviolet (UV) light.

BACKGROUND

Ultraviolet (UV) light is useful, for example, for initiating free radical reaction chemistries used in coatings, adhesives, and polymeric materials. Ultraviolet light is also useful, for example, for disinfecting surfaces, filters, bandages, membranes, articles, air, and liquids (e.g., water). Examples where UVC (i.e., ultraviolet C includes wavelengths in a range from 100 nanometers to 280 nanometers) disinfection could be applied include medical offices and supplies, airplane restrooms, hospital rooms and surgical equipment, schools, air and water purification, and consumer applications (e.g., toothbrush and cell phone disinfection). Prevention of infection and spread of disease, especially in high-risk environments and populations, has become increasingly more critical as pathogens mutate and develop antibiotic resistance. The availability and speed of global human travel elevates risks of rapidly developed epidemics/pandemics. Air and water disinfection is paramount to human health and preventing infectious disease. Benefits of UVC disinfection include touch-free application, and the mechanical disruption of cells at non-gene specific targets is unlikely to be overcome by pathogens via mutation to develop resistance. Surfaces being disinfected with ultraviolet light other than metal, ceramic, or glass surfaces will need protection from ultra-violet light. UVC irradiation can be applied to effectively inactivate or kill prokaryotic and eukaryotic microorganisms alike, including bacteria, viruses, fungi and molds. Bacterial strains with developed resistance to one or more antibiotics are also susceptible to UVC light. Some examples of pathogens of heightened interest include hospital acquired infections (e.g., C. diff, *E. coli*, MRSA, *Klebsiella*, influenza, mycobacteria, and enterobacteria), water and soil borne infections (e.g., giardia, *legionella*, and *campylobacter*) and airborne infections (e.g., influenza, pneumonia, and tuberculosis).

UV light, however, can also be harmful to people and animals in varying degrees. For example, UV light sources that emit 400 nm to 500 nm wavelength light may cause long term damage to the eyes.

SUMMARY

In a first aspect, a multilayer article is provided. The multilayer article includes an absorbent layer that absorbs at least 50, 60, 70, 80, 90, or 95 percent of incident ultraviolet light having a wavelength between at least 230 nanometers and 400 nanometers. The absorbent layer has a major surface. The multilayer article further includes an ultraviolet mirror adjacent to the major surface of the absorbent layer. The ultraviolet mirror is comprised of at least a plurality of alternating first and second optical layers collectively reflecting at an incident light angle of at least one of 0°, 15°, 30°, 45°, 60°, or 75°, at least 50, 60, 70, 80, 90, or 95 percent of incident ultraviolet light in a wavelength range from 190 nanometers, 195 nm, or 200 nm, to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers.

In a second aspect, a system is provided. The system includes a broadband UVC light source; and the multilayer article according to the first aspect.

In a third aspect, a device is provided. The device includes a chamber including at least one wall; a broadband UVC light source located within the chamber; an absorbent layer adjacent to the at least one wall of the chamber; and an ultraviolet mirror located within the chamber between the broadband UVC light source and the absorbent layer. The ultraviolet mirror is comprised of at least a plurality of alternating first and second optical layers collectively reflecting at an incident light angle of at least one of 0°, 15°, 30°, 45°, 60°, or 75°, at least 50, 60, 70, 80, 90, or 95 percent of incident ultraviolet light in a wavelength range from 190 nanometers to 230 nanometers and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers to 400 nanometers. At least 50, 60, 70, 80, 90, or 95 percent of ultraviolet light having a wavelength between at least 230 nanometers and 400 nanometers transmitted through the ultraviolet mirror is absorbed in the chamber.

In a fourth aspect, a method of disinfecting at least one material is provided. The method includes obtaining a system according to the second aspect or a device according to the third aspect; directing UVC light from the broadband UVC light source at the ultraviolet mirror; and exposing the at least one material to ultraviolet light in a wavelength range from 190 nanometers to 230 nanometers. The ultraviolet light is reflected by the ultraviolet mirror towards the at least one material. The method is useful, for example, for disinfecting materials such as medical instruments, hygiene articles, air, liquids (e.g., water or beverages), filter media, food preparation devices, and porous membranes.

DETAILED DESCRIPTION

Glossary

Figures 1A, 1B:
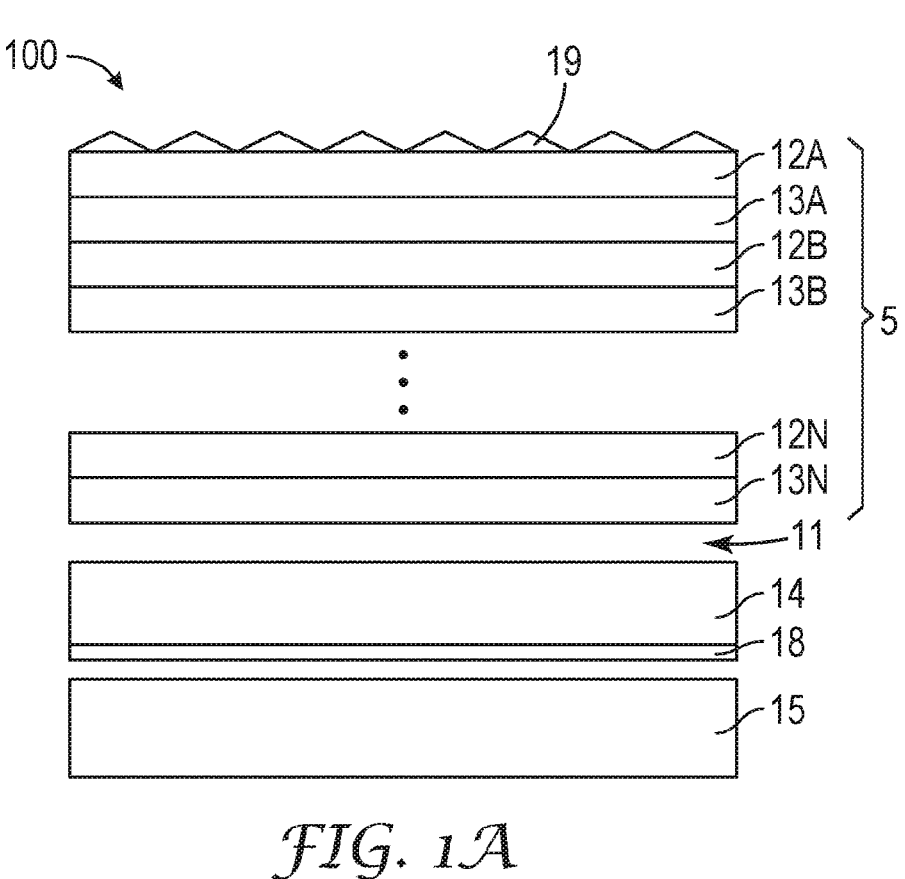
FIGS. 1A-1B are schematic cross-sectional views of two exemplary multilayer articles preparable according to the present disclosure.

As used herein, "fluoropolymer" refers to any organic polymer containing fluorine.

As used herein, "incident" with respect to light refers to the light falling on or striking a material.

As used herein, the term or prefix "micro" refers to at least one dimension defining a structure or shape being in a range from 1 micrometer to 1 millimeter. For example, a micro-structure may have a height or a width that is in a range from 1 micrometer to 1 millimeter.

As used herein, the term or prefix "nano" refers to at least one dimension defining a structure or a shape being less than 1 micrometer. For example, a nano-structure may have at least one of a height or a width that is less than 1 micrometer.

As used herein, "radiation" refers to electromagnetic radiation unless otherwise specified.

As used herein, "absorption" refers to a material convert-ing the energy of light radiation to internal energy.

As used herein, "absorb" with respect to wavelengths of light encompasses both absorption and scattering, as scat-tered light also eventually gets absorbed.

As used herein, "scattering" with respect to wavelengths of light refers to causing the light to depart from a straight path and travel in different directions with different inten-sities.

As used herein, "reflectance" is the measure of the pro-portion of light or other radiation striking a surface at normal incidence which is reflected off it. Reflectivity typically varies with wavelength and is reported as the percent of incident light that is reflected from a surface (0 percent—no reflected light, 100—all light reflected. Reflectivity and reflectance are used interchangeably herein.

As used herein, "reflective" and "reflectivity" refer to the property of reflecting light or radiation, especially reflec-tance as measured independently of the thickness of a material.

As used herein, "average reflectance" refers to reflectance averaged over a specified wavelength range.

Absorbance can be measured with methods described in ASTM E903-12 "Standard Test Method for Solar Absorp-tance, Reflectance, and Transmittance of Materials Using Integrating Spheres". Absorbance measurements described herein were made by making transmission measurements as previously described and then calculating absorbance using Equation 1.

As used herein, the term "absorbance" with respect to a quantitative measurement refers to the base 10 logarithm of a ratio of incident radiant power to transmitted radiant power through a material. The ratio may be described as the radiant flux received by the material divided by the radiant flux transmitted by the material. Absorbance (A) may be calcu-lated based on transmittance (T) according to Equation 1:

$$A = -\log_{10} T \qquad (1)$$

Emissivity can be measured using infrared imaging radi-ometers with methods described in ASTM E1933-14 (2018) "Standard Practice for Measuring and Compensating for Emissivity Using Infrared Imaging Radiometers."

Multilayer Articles

In a first aspect, a multilayer article is provided. The multilayer article comprises:

a) an absorbent layer that absorbs at least 50, 60, 70, 80, 90, or 95 percent of incident ultraviolet light having a wavelength between at least 230 nanometers and 400 nanometers, the absorbent layer comprising a major surface; and b) an ultraviolet mirror adjacent to the major surface of the absorbent layer, wherein the ultraviolet mirror is comprised of at least a plurality of alternating first and second optical layers collectively reflecting at an inci-dent light angle of at least one of 0°, 15°, 30°, 45°, 60°, or 75°, at least 50, 60, 70, 80, 90, or 95 percent of incident ultraviolet light in a wavelength range from 190 nanometers to 240 nanometers and collectively transmitting at an incident light angle of at least one of 0°, 15°, 30°, 45°, 60°, or 75°, at least 50, 60, 70, 80, 90, or 95 percent of incident ultraviolet light in a wave-length range from greater than 240 nanometers to 400 nanometers.

It may alternatively be desired for the ultraviolet mirror to reflect ultraviolet light having a somewhat different wave-length range than 190 nm to 240 nm and to transmit ultraviolet light at a concomitantly different wavelength range than greater than 240 nm to 400 nm. For instance, in some embodiments, the ultraviolet mirror reflects ultraviolet light in a wavelength range of 190 nm or 200 nm to any of 230 nm, 235 nm, or 240 nm; such as from 190 nm to 230 nm, from 200 nm to 240 nm, or from 200 nm to 230 nm. In such embodiments, the ultraviolet mirror transmits ultraviolet light in a wavelength range greater than the upper limit of the wavelength range that is reflected, i.e., greater than 230 nm, greater than 235 nm, or greater than 240 nm. For each of these wavelengths/wavelength ranges, it is to be under-stood that the ultraviolet mirror is exposed to incident light angle of at least one of 0°, 15°, 30°, 45°, 60°, or 75°, and the optical layers collectively reflect at least 50, 60, 70, 80, 90, or 95 percent of the incident ultraviolet light in the specified wavelength range; and collectively transmits at an incident light angle of at least one of 0°, 15°, 30°, 45°, 60°, or 75°, at least 50, 60, 70, 80, 90, or 95 percent of incident ultraviolet light in the specified wavelength range.

It is to be understood that the percent of incident light absorbed refers to the amount absorbed integrated over a particular wavelength range (as opposed to the amount of a single wavelength that is absorbed).

Advantageously, the combination of the absorbent layer and the ultraviolet mirror in the multilayer article enables the use of a broadband UV light source to ultimately provide a relatively narrow band of UVC light (e.g., ranging from 190 nanometers to 240 nanometers). This is accomplished by 1) the ultraviolet mirror i) reflecting light having a wavelength ranging from 190 nm to as much as 240 nm and ii) transmitting light having a wavelength ranging from greater than the maximum wavelength of the reflecting range to 400 nm; and 2) the absorbent layer absorbing light having a wavelength ranging from 230 nm to 400 nm. As indicated above, typically the absorption, transmission, and/or reflec-tion is less than 100% of the total incident light. In most preferred embodiments, greater than 90 percent, 91, 92, 93, 94, 95, 96, 97, or 98 or greater, of incident light is absorbed, transmitted, and/or reflected. Wavelengths of light below 230 nm have not been found to be carcinogenic to human skin, thus the reflection of 190 nm to 230 nm by the ultraviolet mirror can assist in disinfection with less risk to humans in the vicinity. Wavelengths of light between 240 nm and 230 nm may also be acceptable in some applications. In some embodiments, the multilayer article has a UV reflectivity greater than 90% (in some embodiments, greater than 99%), specifically of at least a wavelength of 222 nm.

The absorbent layer preferably resists ultraviolet light-induced damage/degradation over time by absorbing ultra-violet light that may pass through the ultraviolet mirror. Ultraviolet light, in particular the ultraviolet radiation hav-ing wavelengths in a range from 280 nm to 400 nm, can induce degradation of plastics, which in turn results in color change and deterioration of optical and mechanical proper-ties. Inhibition of photo-oxidative degradation is important, for instance, for outdoor applications wherein long-term durability is mandatory. The absorption of ultraviolet light by polyethylene terephthalates, for example, starts at around 360 nm, increases markedly below 320 nm, and is very pronounced at below 300 nm. Polyethylene naphthalates strongly absorb ultraviolet light in the 310 nm to 370 nm range, with an absorption tail extending to about 410 nm, and with absorption maxima occurring at 352 nm and 337 nm. Chain cleavage occurs in the presence of oxygen, and the predominant photooxidation products are carbon monoxide, carbon dioxide, and carboxylic acids. Besides the direct photolysis of the ester groups, consideration has to be given to oxidation reactions, which likewise form carbon dioxide via peroxide radicals.

In general, the absorbent layer may include any polymeric composition (i.e., polymer plus additives) that is capable of withstanding ultraviolet light radiation for an extended period of time, while absorbing (including scattering) ultraviolet radiation. In some embodiments, the absorbent layer comprises a silicone thermoplastic, a fluoropolymer, copolymers thereof, or blends thereof. In some embodiments, the absorbent layer comprises a fluoropolymer (co)polymer comprising polymerized units derived from one or more monomers selected from tetrafluoroethylene, hexafluoropropylene, vinylidene fluoride, a perfluoroalkoxy alkylene, or a combination thereof. In this context, the term "polymer" will be understood to include homopolymers and copolymers, as well as polymers or copolymers that may be formed in a miscible blend, for example, by coextrusion or by reaction, including transesterification. The terms "polymer" and "copolymer" also include both random and block copolymers. These polymers, suitable for the absorbent layer, tend to exhibit less degradation from exposure to ultraviolet radiation (e.g., wavelengths between 190 nm and 400 nm) than other polymers formed of different monomers.

In some embodiments, the absorbent layer comprises one or more of an ultraviolet radiation absorber, an ultraviolet radiation scatterer, a hindered amine light stabilizer, an anti-oxidant, a pigment, or a combination thereof. Suitable ultraviolet radiation absorbers include carbon black, titanium dioxide, zinc oxide, cesium dioxide, zirconium dioxide, or combinations thereof. These particular ultraviolet radiation absorbers tend to be stable to ultraviolet radiation in addition to absorbing the radiation. Suitable ultraviolet radiation absorbers further include a benzotriazole compound, a benzophenone compound, a triazine compound (e.g., including any combination thereof).

Some suitable ultraviolet radiation absorbers are red shifted UV absorbers (RUVA) which absorb at least 70% (in some embodiments, at least 80%, or even greater than 90%) of the UV light in the wavelength region from 180 nm to 400 nm. Typically, it is desirable if the RUVA is highly soluble in polymers of the absorbent layer, highly absorptive, photopermanent and thermally stable in the temperature range from 200° C. to 300° C. for extrusion process to form the protec.

RUVAs typically have enhanced spectral coverage in the long-wave UV region, enabling it to block the high wavelength UV light that can cause yellowing in polyesters. Typical UV protective layers have thicknesses in a range from 13 micrometers to 380 micrometers (0.5 mil to 15 mils) with a RUVA loading level of 2-10 wt. %. One of the most effective RUVA is a benzotriazole compound, 5-trifluoromethyl-2-(2-hydroxy-3-alpha-cumyl-5-tert-octylphenyl)-2H-benzotriazole (available under the trade designation "CGL-0139" from BASF, Florham Park, NJ). Other exemplary benzotriazoles include 2-(2-hydroxy-3,5-di-alpha-cumylphehyl)-2H-benzotriazole, 5-chloro-2-(2-hydroxy-3-tert-butyl-5-methylphenyl)-2H-benzotiazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-alpha-cumyl-5-tert-octylphenyl)-2H-benzotriazole, 2-(3-tert-butyl-2-hydroxy-5-methylphenyl)-5-chloro-2H-benzotriazole. Further exemplary RUVAs includes 2(-4,6-diphenyl-1-3,5-triazin-2-yl)-5-hexyloxy-phenol. Other exemplary UV absorbers include those available from BASF under the trade designations "TINUVIN 1577," "TINUVIN 900," "TINUVIN 1600," and "TINUVIN 777." Other exemplary UV absorbers are available, for example, in a polyester master batch under the trade designation "TA07-07 MB" from Sukano Polymers Corporation, Dunkin, SC. An exemplary UV absorber for polymethylmethacrylate is a masterbatch available, for example, under the trade designation "TA11-10 MBO1" from Sukano Polymers Corporation. An exemplary UV absorber for polycarbonate is a masterbatch from Sukano Polymers Corporation, under the trade designations "TA28-09 MB01." In addition, the UV absorbers can be used in combination with hindered amine light stabilizers (HALS) and anti-oxidants. Exemplary HALS include those available from BASF, under the trade designation "CHIMASSORB 944" and "TINUVIN 123." Exemplary anti-oxidants include those obtained under the trade designations "IRGANOX 1010" and "ULTRANOX 626", also available from BASF.

In select embodiments, the absorbent layer further absorbs at least 30 percent, 40, 50, 60, 70, 80, or at least 90 percent of incident visible light having a wavelength between at least 400 nm and 700 nm. Typically, there is no need for the multilayer article to be transparent to visible light, thus it can be preferred for the absorbent layer to absorb 70 percent or greater of incident visible light having a wavelength between at least 400 nm and 700 nm to minimize reflection of visible light back out of the multilayer article.

In select embodiments, the absorbent layer reflects at least 30 percent, at least 40 percent, at least 50 percent, at least 60 percent, at least 70 percent, at least 80 percent, or at least 90 percent of incident visible light having a wavelength between at least 400 nanometers and 700 nanometers.

The ultraviolet mirror comprises multiple low/high index pairs of film layers, wherein each low/high index pair of layers has a combined optical thickness of ½ the center wavelength of the band it is designed to reflect. Stacks of such films are commonly referred to as quarterwave stacks. In some embodiments, different low/high index pairs of layers may have different combined optical thicknesses, such as where a broadband reflective optical film is desired. Materials employed in the ultraviolet mirrors are preferably resistant to ultraviolet radiation. Many fluoropolymers and certain inorganic materials are resistant to ultraviolet radiation.

In some embodiments of the ultraviolet mirrors described herein, the at least first optical layer comprises inorganic material (e.g., at least one of zirconium oxynitride, hafnia, alumina, magnesium oxide, yttrium oxide, lanthanum fluoride, or neodymium fluoride), and wherein the second optical layer comprises inorganic material (e.g., at least one of silica, aluminum fluoride, magnesium fluoride, calcium fluoride, silica alumina oxide, or alumina doped silica). Exemplary materials are available, for example, from Materion Corporation, Mayfield Heights, OH, and Umicore Corporation, Brussels, Belgium.

In some embodiments of the ultraviolet mirrors described herein, the at least first optical layer comprises a polymeric material (e.g., at least one of polyvinylidene fluoride (PVDF), ethylene tetrafluoroethylene (ETFE)), and the second optical layer comprises polymeric material (e.g., at least one of a copolymer (THV) or a polyethylene copolymer comprising subunits derived from tetrafluoroethylene (TFE), hexafluoropropylene (HFP), and vinylidene fluoride (VDF), a copolymer (FEP) comprising subunits derived from tetrafluoro-ethylene (TFE) and hexafluoropropylene (HFP), or perfluoroalkoxy alkane (PFA)).

Second optical layers can comprise fluorinated copolymers materials such as at least one of fluorinated ethylene propylene copolymer (FEP); copolymers of tetrafluoroethylene, hexafluoropropylene, and vinylidene fluoride (THV); copolymers of tetrafluoroethylene, hexafluoropropylene, or ethylene. Particularly useful are melt processable copolymers of tetrafluoroethylene and at least two, or even at least three, additional different comonomers.

In some embodiments, the first optical layer is a fluoropolymer and the second optical layer is a fluoropolymer. Examples of the materials that are desirable for such embodiments include ETFE/THV, PMMA/THV, PVDF/FEP, ETFE/FEP, PVDF/PFA, and ETFE/PFA. In select embodiments, the at least first optical layer comprises at least one of polyvinylidene fluoride or ethylene tetrafluoroethylene (ETFE) and the second optical layer comprises a copolymer of tetrafluoroethylene, hexafluoropropylene, and vinylidene fluoride (THV).

Exemplary melt processable copolymers of tetrafluoroethylene and other monomers discussed above include those available as copolymers of tetrafluoroethylene, hexafluoropropylene, and vinylidene fluoride under the trade designations "DYNEON THV 220," "DYNEON THV 230," "DYNEON THV 2030," "DYNEON THV 500," "DYNEON THV 610," and "DYNEON THV 815" from Dyneon LLC, Oakdale, MN; "NEOFLON EFEP" from Daikin Industries, Ltd., Osaka, Japan; "AFLAS" from Asahi Glass Co., Ltd., Tokyo, Japan; and copolymers of ethylene and tetrafluoroethylene available under the trade designations "DYNEON ET 6210A" and "DYNEON ET 6235" from Dyneon LLC; "TEFZEL ETFE" from E.I. duPont de Nemours and Co., Wilmington, DE; and "FLUON ETFE" by Asahi Glass Co., Ltd.

Ultraviolet mirrors described herein can be made using general processing techniques, such as by coextrusion of alternating polymer layers having different refractive indices, for example, as described in U.S. Pat. No. 5,882,774 (Jonza et al.); 6,045,894 (Jonza et al.); 6,368,699 (Gilbert et al.); 6,531,230 (Weber et al.); 6,667,095 (Wheatley et al.); 6,783,349 (Neavin et al.); 7,271,951 B2 (Weber et al); U.S. Pat. No. 7,632,568 (Padiyath et al.); U.S. Pat. No. 7,652,736 (Padiyath et al.); and U.S. Pat. No. 7,952,805 (McGurran et al.); and PCT Publications WO 95/17303 (Ouderkirk et al.) and WO 99/39224 (Ouderkirk et al.).

Desirable techniques for providing an ultraviolet mirror with a controlled spectrum include the use of an axial rod heater control of the layer thickness values of coextruded polymer layers as described, for example, in U.S. Pat. No. 6,783,349 (Neavin et al.); timely layer thickness profile feedback during production from a layer thickness measurement tool such as an atomic force microscope (AFM), a transmission electron microscope, or a scanning electron microscope; optical modeling to generate the desired layer thickness profile; and repeating axial rod adjustments based on the difference between the measured layer profile and the desired layer profile.

The basic process for layer thickness profile control involves adjustment of axial rod zone power settings based on the difference of the target layer thickness profile and the measured layer profile. The axial rod power increase needed to adjust the layer thickness values in a given feedblock zone may first be calibrated in terms of watts of heat input per nanometer of resulting thickness change of the layers generated in that heater zone. For example, fine control of the spectrum is possible using 24 axial rod zones for 275 layers. Once calibrated, the necessary power adjustments can be calculated once given a target profile and a measured profile. The procedure is repeated until the two profiles converge.

The layer thickness profile (layer thickness values) of ultraviolet mirrors described herein reflecting at least 50 percent of incident UV light over a specified wavelength range can be adjusted to be approximately a linear profile with the first (thinnest) optical layers adjusted to have about a ¼ wave optical thickness (index times physical thickness) for 190 nm light and progressing to the thickest layers which would be adjusted to be about ¼ wave thick optical thickness for 240 nm light or 230 nm light.

Dielectric mirrors, with optical thin film stack designs comprised of alternating thin layers of inorganic dielectric materials with refractive index contrast, are particularly suited for this. In recent decades they are used for applications in UV, Visible, NIR and IR spectral regions. Depending upon the spectral region of interest, there are specific materials suitable for that region. Also, for coating these materials, one of two forms of physical vapor deposition (PVD) are used: evaporation or sputtering. Evaporated coatings rely upon heating the coating material (evaporant) to a temperature at which it evaporates. This is followed by condensation of the vapor upon a substrate. For evaporated dielectric mirror coatings, the electron-beam deposition process is most commonly used. Sputtered coatings use energetic gas ions to bombard a material ("target") surface, ejecting atoms which then condense on the nearby substrate. Depending upon which coating method is used, and the settings used for that method, thin film coating rate and structure-property relationships will be strongly influenced. Ideally, coating rates should be high enough to allow acceptable process throughput and film performance, characterized as dense, low stress, void free, non-optically absorbing coated layers.

Exemplary embodiments can be designed to have peak reflectance at 222 nm, by both PVD methods. For example, coating discrete substrates by electron-beam deposition method, using $HfO_2$ as the high refractive index material and $SiO_2$ as the low refractive index material. Mirror design has alternating layers of "quarter wave optical thickness" (qwot) of each material, that are coated, layer by layer until, for example, after 11 layers the reflectance at 215 nm is >95%. The bandwidth of this reflection peak is around 50 nm. Quarter wave optical thickness is the design wavelength, here 215 nm, divided by 4, or 53.75 nm. Physical thickness of the high refractive index layers ($HfO_2$) is the quotient of qwot and refractive index of $HfO_2$ at 215 nm (2.35), or 23.2 nm. Physical thickness of the low refractive index layers ($MgF_2$), with 215 nm refractive index at 1.42, is 37.85 nm. Coating a thin film stack, then, which is comprised of alternating layers of $HfO_2$ and $SiO_2$ and designed to have peak reflectance at 215 nm begins by coating layer 1 $HfO_2$ at 23.2 nm. In electron beam deposition a four-hearth evaporation source is used. Each hearth is cone-shaped and 17 $cm^3$ volume of $HfO_2$ chunks fill it. The magnetically deflected high voltage electron beam is raster scanned over the material surface as filament current of the beam is steadily, in a pre-programmed fashion, increased. Upon completion of the pre-programmed step the $HFO_2$ surface is heated to evaporation temperature, about 2500° C., and a source shutter opens, the $HfO_2$ vapor flux emerging from the source in a cosine-shaped distribution and condensing upon the substrate material above the source. For enhancement of coating uniformity, the substrate holders rotate during deposition. Upon reaching the prescribed coating thickness (23.2 nm) the filament current shuts off; the shutter closes and the HfO₂ material cools. For layer 2 the evaporation source is then rotated to a hearth containing chunks of MgF₂ and a similar pre-programmed heating process begins. Here, the MgF₂ surface temperature is about 950° C. when the source shutter opens and, upon reaching the prescribed coating thickness (37.85 nm), the filament current shuts off; the shutter closes and the HfO₂ material cools. This step-wise process is continued, layer by layer, until the total number of design layers is reached. With this optical design, as total layers are increased, from 3 to 11, the resulting peak reflectance increases accordingly, from 40% at 3 layers to >95% at 11 layers.

Optionally, ultraviolet mirrors can be prepared in continuous roll to roll (R2R) fashion, using ZrON as the high refractive index material and SiO₂ as the low refractive index material. The optical design is the same type of thin film stack, alternating qwot layers of the two materials. For ZrON, with refractive index at 215 nm of 3.1, the physical thickness target was 17.3 nm. For SiO₂, here sputtered from an aluminum-doped silicon sputter target, with refractive index 1.61, the target thickness was 33.3 nm. Layer one ZrON is DC sputtered from a pure zirconium sputter target in a gas mixture of argon, oxygen and nitrogen. Whereas argon is the primary sputtering gas, oxygen and nitrogen levels are set to achieve transparency, low absorptance and high refractive index. The film roll transport initially starts at a pre-determined speed, and the sputter source power is ramped to full operating power, followed by introduction of the reactive gases and then achieving steady state condition. Depending upon the length of film to coat, the process continues until total footage is achieved. Here, as the sputter source is orthogonal to and wider than the film which is being coated, the uniformity of coating thickness is quite high. Upon reaching the desired length of coated film the reactive gases are set to zero and the target is sputtered to a pure Zr surface state. The film direction is next reversed and silicon (aluminum doped) rotary pair of sputter targets has AC frequency (40 kHz) power applied in an argon sputtering atmosphere. Upon reaching steady state, oxygen reactive gas is introduced to provide transparency and low refractive index. At the pre-determined process setting and line speed the second layer is coated over the length which was coated for layer one. Again, as these sputter sources are also orthogonal to and wider than the film being coated, the uniformity of coating thickness is quite high. After reaching the desired length of coated film the reactive oxygen is removed and the target is sputtered in argon to a pure silicon (aluminum doped) surface state. Layers three to five or seven or nine or eleven or thirteen, depending upon peak reflectance target, are coated in this sequence. Upon completion, the film roll is removed for post-processing.

For manufacturing of these inorganic coatings, the electron beam process is best suited for coating discrete parts. Though some chambers have demonstrated R2R film coating, the layer by layer coating sequence would still be necessary. For R2R sputtering of film, it is advantageous to use a sputtering system with multiple sources located around one, or perhaps two, coating drums. Here, for a thirteen layers optical stack design, a two, or even single, machine pass process, with alternating high and low refractive index layers coated sequentially, would be feasible. How many machine passes needed would be contingent upon machine design, cost, practicality of thirteen consecutive sources, and so forth. Additionally, coating rates would need to be matched to a single film line speed.

Preferably, the ultraviolet mirror reflects at an incident light angle of at least one of 0°, 15°, 30°, 45°, 60°, or 75°, at least 80 percent, 85, 90, 91, 92, 93, 94, 95, 96, 97, or at least 98 percent of incident ultraviolet light in a wavelength range from 200 nanometers to 230 nanometers. The selection of the material combinations used in creating the ultraviolet mirror depends, for example, upon the desired bandwidth that will be reflected. Higher refractive index differences between the first optical layer polymer and the second optical layer polymer create more optical power thus enabling more reflective bandwidth per pair of layers. The number of optical layers is selected to achieve the desired optical properties using the minimum number of layers for reasons of film thickness, flexibility and economy. In the case of reflective films such as mirrors, the number of layers is preferably less than about 2,000, more preferably less than about 1,000, and even more preferably less than about 750. In some embodiments, the number of layers is at least 100, 125, 150, 175, or at least 200. The refractive index of zirconia, however, is so high that a much lower number of optical layers is needed when zirconia or zirconia oxynitride is employed, such as 50 optical layers or less, 40, 30, 20, or 15 optical layers or less; and 3 optical layers or more, 5, 7, or 10 optical layers or more, may be needed.

In some embodiments, the ultraviolet mirror has a reflection spectrum at an incident light angle of 0° (e.g., normal incidence) that shifts to shorter wavelengths at oblique angles (e.g., 15°, 30°, 45°, 60°, or 75°). One can thus prepare an ultraviolet mirror having a normal incidence spectrum such that at an intended angle of incidence, the ultraviolet mirror reflects ultraviolet light in a range of 190 nm to 240 nm. Optionally, an intervening optical element (e.g., prism, louver, or the like) is placed between the ultraviolet mirror and a UVC light source to change or limit the angle of incidence of the light emitted by the UVC light source before it reaches an exterior surface of the ultraviolet mirror. Moreover, one can form a shape of an exterior surface of the ultraviolet mirror such that the angle of incidence is maintained for various locations of the ultraviolet mirror.

In some embodiments, the ultraviolet mirror absorbs at an incident light angle of at least one of 0°, 15°, 30°, 45°, 60°, or 75°, at least 30 percent, 40, 50, 60, 70, 80, 90 percent, at least 95 percent, or at least 98 percent of incident visible light having a wavelength between at least 400 nm and 700 nm. Optionally, a pigment or a dye can be included in the ultraviolet mirror to absorb one or more wavelengths from 400 nm to 700 nm. Suitable pigments may include for instance, metal oxides such as, for example, antimony tin oxide, indium tin oxide, cesium oxides, iron oxides, and cuprous oxides. As mentioned above with respect to the absorbent layer, there is typically no need for the multilayer article to be transparent to visible light, thus it can be preferred for the ultraviolet mirror to absorb 30 percent or greater of incident visible light having a wavelength between at least 400 nm and 700 nm to minimize reflection of visible light back out of the multilayer article.

Referring to FIGS. 1A and 1i, schematic cross-sectional views are provided of two exemplary multilayer articles 10, each including an ultraviolet mirror 5 comprising first optical layers 12A, 12B, 12N, second optical layers 13A, 13B, 13N and an absorbent layer 14 adjacent to the ultraviolet mirror.

In some embodiments, a major surface of the absorbent layer 14 is in direct contact with a major surface of the ultraviolet mirror 5. In other embodiments, the multilayer article 10 comprises an air gap 11 disposed between the absorbent layer 14 and the ultraviolet mirror 5, as shown in the figures. For instance, an air gap can be achieved by taping the edges of the absorbent layer to the ultraviolent mirror. Attaching the two layers using adhesive tape also enables using an ultraviolet mirror having a shape that is different than the shape of the absorbent layer.

Referring to FIG. 1A, the multilayer article 10 optionally further comprises an adhesive layer 15 adjacent to the absorbent layer 14, wherein the absorbent layer 14 is disposed between the ultraviolet mirror 5 and the adhesive layer 15. An adhesive could be useful for attaching the multilayer article to a substrate (e.g., a wall, a ceiling, a device housing, etc.). Such optional adhesive layers may comprise any adhesive (e.g., thermosetting adhesive, hot melt adhesive, and/or pressure-sensitive adhesive). If present, an optional adhesive layer preferably comprises a pressure-sensitive adhesive. In some embodiments, the adhesive may be resistant to ultraviolet radiation damage. Exemplary adhesives which are typically resistant to ultraviolet radiation damage include silicone adhesives and acrylic adhesives containing UV-stabilizing/blocking additive(s), for example, as discussed hereinabove. The optional adhesive layer may comprise thermally-conductive particles to aid in heat transfer. Exemplary thermally-conductive particles include aluminum oxide particles, alumina nanoparticles, aluminum trihydrate, aluminum coated glass beads, metal silicides, graphite, graphene, carbon nanotubes, hexagonal boron nitride particles and agglomerates (e.g., available as 3M BORON DINITRIDE from 3M Company), graphene particles, graphene oxide particles, metal particles, and combinations thereof. Further, optional releasable liners used with an optional adhesive layer may comprise, for example, a polyolefin film, a fluoropolymer film, a coated PET film, or a siliconized film or paper.

Referring to FIG. 1B, the multilayer article optionally further comprises one or more of a heat transfer layer 16, a plurality of heat transfer fins 17, or a plurality of heat transfer pins 17, adjacent to a major surface 4 of the absorbing layer 14 and opposite the ultraviolet mirror 5. Suitable materials of which the heat transfer layer, fins, and/or pins may be composed includes metals such as aluminum, silver, gold, copper, nickel, iron, steel, or titanium. The heat transfer layer, plurality of heat transfer fins, or plurality of heat transfer pins, may comprise a polymer filled with thermally-conductive particles including; aluminum oxide particles, alumina nanoparticles, aluminum trihydrate, aluminum coated glass beads, metal silicides, graphite, graphene, carbon nanotubes, hexagonal boron nitride particles and agglomerates (e.g., available as 3M BORON DINITRIDE from 3M Company), graphene particles, graphene oxide particles, metal particles, and combinations thereof.

Referring again to each of FIGS. 1A-1B, additional optional features are provided. For instance, in some embodiments, an (e.g., outer) major surface of the ultraviolet mirror 5 may comprise a plurality of nonplanar features 19 protruding from the major surface. Any shape of nonplanar features may be suitable, (e.g., prisms, ridges, linear and/or curved polygons). In the embodiment shown, the nonplanar features 19 have a shape of a triangular prism. Such nonplanar features may be micro-structured and/or nano-structured over some or all of its surface; for example, as described in PCT International Application Publication No. WO 2019/130198 (Hebrink et al.). In some embodiments, the nano-structure may be superimposed on the micro-structure on the surface of the ultraviolet mirror. The micro-structures may be arranged as a series of alternating micro-peaks and micro-spaces. The size and shape of the micro-spaces between micro-peaks may mitigate the adhesion of dirt particles to the micro-peaks. The nano-structures may be arranged as at least one series of nano-peaks disposed on at least the micro-spaces. The micro-peaks may be more durable to environmental effects than the nano-peaks. Because the micro-peaks are spaced only by a micro-space, and the micro-spaces are significantly taller than the nano-peaks, the micro-peaks may serve to protect the nano-peaks on the surface of the micro-spaces from abrasion. Moreover, the nonplanar features may act as light diffusive structures by scattering UVC light reflected from the ultraviolet mirror.

In some embodiments, the ultraviolet mirror may comprise structures specifically for providing light diffusion, for instance when the reflected light is being directed into an area (e.g., a room) in which people may be present. Such light diffusive structures may be provided by including inorganic particles. For example, each structure may correspond to one inorganic particle. The inorganic particles may be dispersed in or disposed on at least one layer of the ultraviolet mirror. The inorganic particles may comprise titania, silica, zirconia, or zinc oxide. The inorganic particles may be in the form of beads or microbeads. The inorganic particles may be formed of a ceramic material, glass, or various combinations of thereof. In some embodiments, the inorganic particles have an effective $D_{90}$ particle size of at least 1 (in some embodiments, at least 3, 5, 6, 7, 8, 9, 10, or even at least 20) micrometers. In some embodiments, the inorganic particles have an effective $D_{90}$ particle size of at most 40 (in some embodiments, at most 25, 20, 15, 14, 13, 12, 11, 10, 9, or even at most 8) micrometers. Surface structures may also include cross-linked polymer beads such as those under the tradename "CHEMISNOW" available from Soken Chemical & Engineering Company, Tokyo, Japan. As defined in NIST "Particle Size Characterization", ASTM B15-96 describes $D_{90}$ as the intercept where 90% of the samples mass has particles with a diameter less than the value. For example, a $D_{90}$ of 10 micrometers specifies that 90% of the samples mass includes particles with diameters less than 10 micrometers.

In some embodiments, the absorbent layer 14 comprises a continuous metal coating or layer 18. Suitable coating or layer thicknesses include 50 nm or greater, 55 nm, 60 nm, 65 nm, 70 nm, or 75 nm or greater; and 100 nm or less, 95 nm, 90 nm, 85 nm, or 80 nm or less. In some embodiments, the continuous metal coating or layer is the entire absorbent layer 14, whereas in the embodiment shown in FIGS. 1A-1B, the continuous metal coating or layer is used in combination with a polymeric absorbent material. In some embodiments, the absorbent layer comprises metal particles disposed in a polymer matrix (not shown). The size of the metal particles is not particularly limited, and the average particle size of the metal particles can range from 10 nm to 10000 nm (10 micrometers). Suitable metals for use as a coating, a layer, or a plurality of particles, include one or more of silver, gold, copper, nickel, or titanium. Use of metal in certain embodiments can increase the absorption of incident light having a wavelength between at least 400 nm and 700 nm (e.g., visible light). Further, the metal can either scatter or absorb harmful UV radiation thereby reducing damage to thermoplastics. U.S. Pat. No. 5,504,134 (Palmer et al.), for instance, describes attenuation of polymer substrate degradation due to ultraviolet radiation through the use of metal oxide particles in a size range of about 0.001 to about 0.2 micrometers (in some embodiments, about 0.01 micrometers to about 0.15 micrometers) in diameter. U.S.

Pat. No. 5,876,688 (Laundon), describes a method for producing micronized zinc oxide that are small enough to be transparent when incorporated as UV blocking and/or scattering agents in paints, coatings, finishes, plastic articles, cosmetics and the like which are well suited for use in the present invention. These fine particles such as zinc oxide and titanium oxide with particle sizes ranging from 10 nm to 100 nm that can attenuate UV radiation are available, for example, from Kobo Products, Inc., South Plainfield, NJ. Flame retardants may also be incorporated as an additive in an absorbent layer.

Systems

In a second aspect, the present disclosure provides a system. The system comprises:

a) a broadband UVC light source; and b) the multilayer article of the first aspect.

Figure 2:
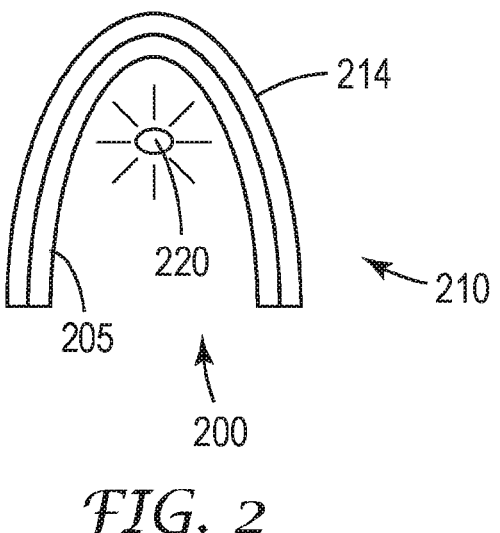
FIG. 2 is a schematic cross-sectional view of an exemplary system preparable according to the present disclosure.

Referring to FIG. 2, a schematic cross-sectional view is provided of an exemplary system 200. The system comprises a broadband UVC light source 220 and a multilayer article 210 according to any of the embodiments of the first aspect, described in detail above. As mentioned above, "UVC" refers to wavelengths of light in a range between 100 nm and 280 nm. Broadband UVC light sources provide a band of wavelengths within this C wavelength range of 30 nm or greater, as opposed to providing a smaller band of wavelengths (e.g., as can be provided by a light emitting diode (LED) light source).

In the embodiment shown in FIG. 2, the multilayer article 210 comprises an absorbent layer 214 directly attached to an ultraviolet mirror 205. Further, the multilayer article 210 comprises a hollow nonplanar shape. Typically, in systems according to the present disclosure, the broadband UVC light source 220 is configured to direct light at the ultraviolet mirror 205 of the multilayer article 210. This allows the ultraviolet mirror 205 to reflect back wavelengths of light in the desirable range (e.g., 190 nm to 240 nm) while transmitting to the absorbent layer 214 and/or absorbing wavelengths of light greater than the maximum of the range (e.g., greater than 240 nm). Preferably, any material that also is directly exposed to emission of light from the broadband UVC light source is located at least 3 centimeters (cm), 3.25 cm, 3.5 cm, 3.75 cm, or at least 4 cm away from the broadband UVC light source to minimize exposure to wavelengths of light that have not been reflected by the ultraviolet mirror 205.

In one exemplary embodiment of a system, a UVC collimator may be provided with a UVC mirror that reflects wavelengths of 200 nm and up to 240 nm (e.g., 230 nm, 235 nm, or 240 nm) and an absorbent layer that absorbs wavelengths of 230 nm or greater to 400 nm. In one use, the system may be employed in a room where people will be present. In such an embodiment, the multilayer article can be attached to the ceiling (i.e., with the absorbent layer disposed between the ceiling and the ultraviolet mirror) and the collimator is tilted upwards toward the ceiling at an angle. For instance, the collimator may be attached to a wall of the room. Light of wavelengths 200 nm to 230 nm (or to 235 nm or 240 nm) is then reflected from the ultraviolet mirror of the multilayer article down onto the people. Light diffusive surface structures can be provided on the UVC mirror film adjacent the ceiling to distribute UVC light in the wavelengths of 200-230 nm more uniformly throughout the room.

More particularly, the system comprises a UVC collimator, a broadband UVC light source, and a multilayer article comprising a UVC mirror and an absorbent layer. The multilayer article is disposed adjacent to a ceiling of a room and the UVC collimator is configured to collimate light from the broadband UVC light source and direct the collimated light at an angle towards the UVC mirror of the multilayer article adjacent to the ceiling. The absorbent layer absorbs at least 50, 60, 70, 80, 90, or 95 percent of incident ultraviolet light having a wavelength between at least 230 nanometers and 400 nanometers. The absorbent layer comprises a major surface and the ultraviolet mirror is adjacent to the major surface of the absorbent layer. The ultraviolet mirror is comprised of at least a plurality of alternating first and second optical layers collectively reflecting at least 50, 60, 70, 80, 90, or 95 percent of incident ultraviolet light in a wavelength range from 200 nm to 230 nanometers, 235 nm, or 240 nm, and collectively transmitting at least 50, 60, 70, 80, 90, or 95 percent of incident ultraviolet light in a wavelength range from greater than 230 nanometers, greater than 235 nm, or greater than 240 nm, to 400 nanometers. Light collimators can be designed to collimate light from a point source can be collimated (focused) using a parabolic (elliptical) reflective optical element. The main requirements are that the source be located near the focal point of the optical element and that the source be relatively small compared with the size of the optical element. Light concentrators can be designed utilizing a surface of revolution generated from a section of an ellipse with the source at one focus and the target at the other focus of the ellipse. The source at one focus shines toward the closest vertex of the ellipse. The section of the ellipse used to generate the surface of revolution is the section defined by the *latus* rectum at the source and the closest vertex to the source. The *latus* rectum must be larger than the source so that the concentrator can collect most of the light from the source. If the source and target were points, all the light from the source would be collected at the target.

Light from a point source can be collimated (focused) using a parabolic (elliptical) reflective optical element, and one suitable collimator for the system comprises a parabolic collimator. The main requirements are that the source be located near the focal point of the optical element and that the source be relatively small compared with the size of the optical element. In most applications, the optical element must be designed for practical considerations such as the size of the light source and the allowed amount of space of the optical element. Given a source diameter Ds (width in 1D) and a design volume consisting of a height Hv and diameter Dv (width in 1D), it is possible to derive an equation for the shape of a near-optimum parabolic reflector:

$$y = a*(x+b)^2 + \text{offset}$$

where $a = Hv/((Dv/2)^2 - (Ds/2)^2)$, $b = -Dv/2$ and offset $= -a \cdot (Ds/2)^2$;

We further need to select Hv and/or Dv such that the focus of the parabola coincides with the location of the light source at [x=Dv/2, y=0], which is achieved by choosing:

$$Hv = ((Dv/2)^2 - (Ds/2)^2)/Ds$$

The resulting optical element is near optimal given the physical constraints of the system. Following the etendue conservation principle, the amount of collimation is proportional to $(Dv/Ds)^2$, with higher design volumes resulting is greater collimation. The cut-off angle of this optical element is given by:

$$\text{Theta} = +/-a \tan((Dv/2+Ds/2)/Hv)$$

In another exemplary embodiment of a system, a UVC reflective chamber may be provided with a UVC mirror that reflects wavelengths of 200 nm and up to 240 nm (e.g., 230 nm, 235 nm, or 240 nm) and an absorbent layer that absorbs wavelengths of 230 nm or greater to 400 nm. In one use, the system may be employed in a room where people will be present. In such an embodiment, the multilayer article can be attached to the ceiling (i.e., with the absorbent layer disposed between the ceiling and the ultraviolet mirror) and the chamber is tilted upwards toward the ceiling at an angle. For instance, the UVC reflective chamber may be attached to a wall of the room. Light of wavelengths 200 nm to 230 nm (or to 235 nm or 240 nm) is then reflected from the ultraviolet mirror of the multilayer article down onto the people. The system comprises a UVC reflective chamber, a broadband UVC light source, and a multilayer article comprising a UVC mirror and an absorbent layer. The multilayer article is disposed adjacent to a ceiling of a room and the UVC chamber is configured to direct light from the broadband UVC light source and direct the UVC light at an angle towards the UVC mirror of the multilayer article adjacent to the ceiling. The absorbent layer absorbs at least 50, 60, 70, 80, 90, or 95 percent of incident ultraviolet light having a wavelength between at least 230 nanometers and 400 nanometers. The absorbent layer comprises a major surface and the ultraviolet mirror is adjacent to the major surface of the absorbent layer. The ultraviolet mirror is comprised of at least a plurality of alternating first and second optical layers collectively reflecting at least 50, 60, 70, 80, 90, or 95 percent of incident ultraviolet light in a wavelength range from 200 nm to 230 nanometers, 235 nm, or 240 nm, and collectively transmitting at least 50, 60, 70, 80, 90, or 95 percent of incident ultraviolet light in a wavelength range from greater than 230 nanometers, greater than 235 nm, or greater than 240 nm, to 400 nanometers. Light diffusive surface structures can be provided on the UVC mirror film adjacent the ceiling to distribute UVC light in the wavelengths of 200-230 nm more uniformly throughout the room.

Suitable broadband UVC light sources for use include any of a low pressure mercury lamp, a medium pressure mercury lamp, a xenon arc lamp, or an excimer lamp. Suitable low pressure mercury lamps include those commercially available from Heraeus-Noblelight (Hanau, Germany), including low pressure mercury amalgam lamps. For instance, a low pressure mercury lamp can provide a peak emission at approximately 254 nm and minimal emission at wavelengths about 245 nm and below as well as about 260 nm and above. Suitable medium pressure mercury lamps include those commercially available from Helios Quartz Americas (Sylvania, OH). Employing a Type 214 quartz sleeve or a synthetic quartz sleeve with a medium pressure mercury lamp can increase the amount of emission at 200 nm to 51% or 89%, respectively. Although the peak emission of medium pressure mercury lamps is at approximately 320 nm, medium pressure mercury lamps are polychromatic and also have several significant emission peaks between about 245 nm and about 300 nm, for instance at approximately 265 nm, as well as a broad emission band between about 210 nm and about 240 nm.

Suitable xenon arc lamps are commercially available from Atlas Material Testing Technology, Inc., (Chicago, IL), Newport (Irvine, CA), and Xenex (San Antonio, TX). Xenon arc lamps tend to have broad emission spectra starting somewhere between about 200 nm and 250 nm, and extending beyond 800 nm, with some minor peaks at about 475 nm and about 775 nm.

Examples of excimer ultraviolet light sources include lamps such as those commercially available from Sterilray (Somersworth, NH) (e.g., krypton chloride UVC lamps with an emission peak at 222 nm), Osram (Massachusetts, United States), Heraeus-Noblelight (Hanau, Germany), Ushio (Tokyo, Japan), and those described in Kogelschatz, Applied Surface Science, 54 (1992), 410-423, glow discharge lamps such as those described in EP Patent Appl. 521,553 (assigned to N. V. Philips), deuterium lamps available from Hamamatsu (Hamamatsu City, Japan), microwave driven lamps such as those described in Kitamura et al, Applied Surface Science, 79/80 (1994), 507-513 and DE 4302555 A1 (assigned to Fusion Systems), and excimer lamps pumped by a volume discharge with ultraviolet preionization as described in Tech. Phys, 39(10), 1054 (1994). Excimer ultraviolet light sources often comprise krypton bromide or krypton chloride. For instance, a deuterium lamp typically has emission spectra showing a broad peak bandwidth between about 200 nm and about 280 nm, then tailing off between about 280 nm to about 700 nm.

Devices

In a third aspect, the present disclosure provides a device. The device comprises:

a) a chamber, the chamber comprising at least one wall;

b) a broadband UVC light source located within the chamber;

c) an absorbent layer adjacent to the at least one wall of the chamber; and d) an ultraviolet mirror located within the chamber between the broadband UVC light source and the absorbent layer, wherein the ultraviolet mirror is comprised of at least a plurality of alternating first and second optical layers collectively reflecting at an incident light angle of at least one of 0°, 15°, 30°, 45°, 60°, or 75°, at least 50, 60, 70, 80, 90, or 95 percent of incident ultraviolet light in a wavelength range from 190 nanometers, 195 nm, or 200 nm, to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers, wherein at least 50, 60, 70, 80, 90, or 95 percent of ultraviolet light having a wavelength between at least 230 nanometers and 400 nanometers transmitted through the ultraviolet mirror is absorbed in the chamber. Accordingly, wavelengths in a range of greater than 230 nm and 400 nm that pass through the ultraviolet mirror can bounce around within the chamber until at least 50 percent of them are eventually absorbed by the absorbent layer and/or the chamber wall. In some embodiments, though, the absorbent layer absorbs at least 10, 20, 30, 40, 50, 60, 70, 80, 90, or 95 percent of incident ultraviolet light having a wavelength between at least 230 nanometers and 400 nanometers.

The ultraviolet mirror and the absorbent layer are according to any of the embodiments of these portions of the multilayer article of the first aspect, described in detail above. The broadband UVC light source is according to any of the embodiments of the broadband UVC light source of the second aspect, described in detail above.

In some embodiments, a chamber for a device is in the form of a cabinet or an enclosure comprising the broadband UVC light source illuminating the interior of the device and the contents of the device with UVC light. The device can be, for example, square, rectangular, conical, parabolic, elliptical, spherical, or a combination of shapes, and includes the ultraviolet mirror present in its interior area. The UV reflection tends to minimize absorption of the desired wavelengths of UVC light before it is absorbed by the microorganisms it is intended for.

Figure 3:
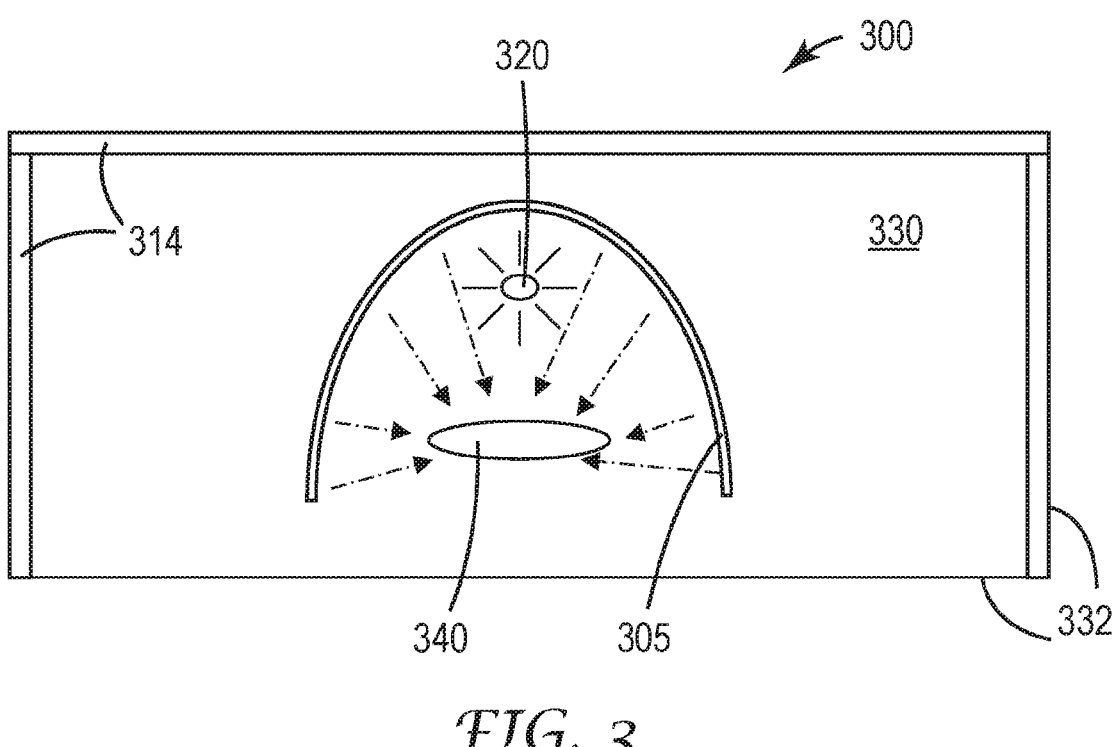
FIG. 3 is a schematic cross-sectional view of an exemplary device preparable according to the present disclosure.

Referring to FIG. 3, a schematic cross-sectional view is provided of one exemplary device 300. The device 300 comprises a chamber 330 comprising at least one wall 332, a broadband UVC light source 320 located within the chamber 330, an absorbent layer 314 adjacent to the at least one wall 332 of the chamber 330, and an ultraviolet mirror 305 located within the chamber 330 between the broadband UVC light source 320 and the absorbent layer 314. Typically, the broadband UVC light source 320 is positioned and/or configured to direct light at the ultraviolet mirror 305.

In this embodiment, the absorbent layer 314 is configured to follow the contours of the at least one wall 332, e.g., is disposed adjacent to the at least one wall 332. In some cases, the absorbent layer 314 is directly adjacent to the at least one wall 332. Optionally, the absorbent layer 314 may be attached to the at least one wall 332, such as by using an adhesive or other fastening means. Additionally, in this embodiment, the ultraviolet mirror 305 is located separate and distanced from the absorbent layer 314. The ultraviolet mirror 305 also has a different shape than the absorbent layer 314, as shown in FIG. 3, where the ultraviolet mirror 305 has a rounded shape and the absorbent layer has a squared-off shape.

The material(s) of which the at least one wall 332 of the chamber 330 are composed are not particularly limited, and may include for instance metal, plastic, ceramic (including glass), concrete, or wood. In certain embodiments, the at least one wall 332 is formed of a heat-resistant or heat-transfer material that can withstand heat generated by absorption of certain wavelengths of light from the broadband UVC light source within the chamber 330. Often, the chamber is configured to be enclosed to contain the wavelengths of light reflected within the chamber, such as by including an access port or door that can be opened to insert or remove a material and closed to shut and/or seal the chamber. When the material is in the form of a liquid or a gas (e.g., in a phase other than a solid), the chamber may be configured to allow a material to be pumped (or otherwise transported) into and out of the chamber for disinfection.

The device 300 is shown containing a material 340 at which the reflected wavelengths of light between 190 nm and 230 nm may be directed, e.g., to disinfect at least a portion of the material 340. Such reflected wavelengths are schematically depicted as dashed arrows in the chamber, pointing towards at least a surface of the material 340. Preferably, any material that is also directly exposed to emission of light from the broadband UVC light source is located at least 3 centimeters (cm), 3.25 cm, 3.5 cm, 3.75 cm, or at least 4 cm away from the broadband UVC light source to minimize exposure to wavelengths of light that have not been reflected by the ultraviolet mirror 305. Some exemplary materials that could be disinfected using the exemplary chamber include for instance, medical instruments, hygiene articles, air, liquids (e.g., water or beverages), filter media, food preparation devices (e.g., a surface, a cutting device, a mixing device, or a cooking device), and porous membranes.

In alternate embodiments that are not shown with the device 300, the ultraviolet mirror and the absorbent layer may be adjacent to each other and/or have essentially the same shape (e.g., similar to the ultraviolet mirror 205 and the absorbent layer 214 illustrated in FIG. 2).

Methods

In a fourth aspect the present disclosure provides a method of disinfecting at least one material. The method comprises:

a) obtaining a system according to the second aspect or a device according to the third aspect;

b) directing UVC light from the broadband UVC light source at the ultraviolet mirror; and c) exposing the at least one material to ultraviolet light in a wavelength range from 190 nanometers to 240 nanometers, the ultraviolet light reflected by the ultraviolet mirror towards the at least one material.

The system is according to any of the embodiments of the system of the second aspect, described in detail above. The device is according to any of the embodiments of the device of the third aspect, described in detail above. The broadband UVC light source is according to any of the embodiments of the broadband UVC light source of the second aspect, described in detail above.

In certain embodiments, step c) above is performed until achievement of a log 2, log 3, log 4, or greater reduction of at least one microorganism on or in the at least one material, as compared to an amount of the at least one microorganism present prior to step c). As used herein, the term "microorganism" refers to any cell or particle having genetic material suitable for analysis or detection (including, for example, bacteria, yeasts, viruses, and bacterial endospores). Log reduction values (LRV) may be determined by measuring the number of colonies of a microorganism present on or in a material prior to disinfection via an exemplary method, disinfecting the material using the method, measuring the number of colonies present on or in the material following disinfection, then calculating the LRV based on colony counts obtained. The method of measuring the number of colony forming units (cfus) on or in a material will vary based on the form of the particular material. For instance, a solid may be swabbed, and a liquid or gas volumetrically sampled (and concentrated if necessary). The cfus may be measured, for instance, using a culture-based method, an imaging detection method, a fluorescence-based detection method, a colorimetric detection method, an immunological detection method, a genetic detection method, or a bioluminescence-based detection method. The LRV is then calculated using the formula below:

$$LRV = (\text{Log of cfus/area or volume of pre-disinfected material}) - (\text{Log of cfus/area or volume of disinfected material})$$

Figure 4:
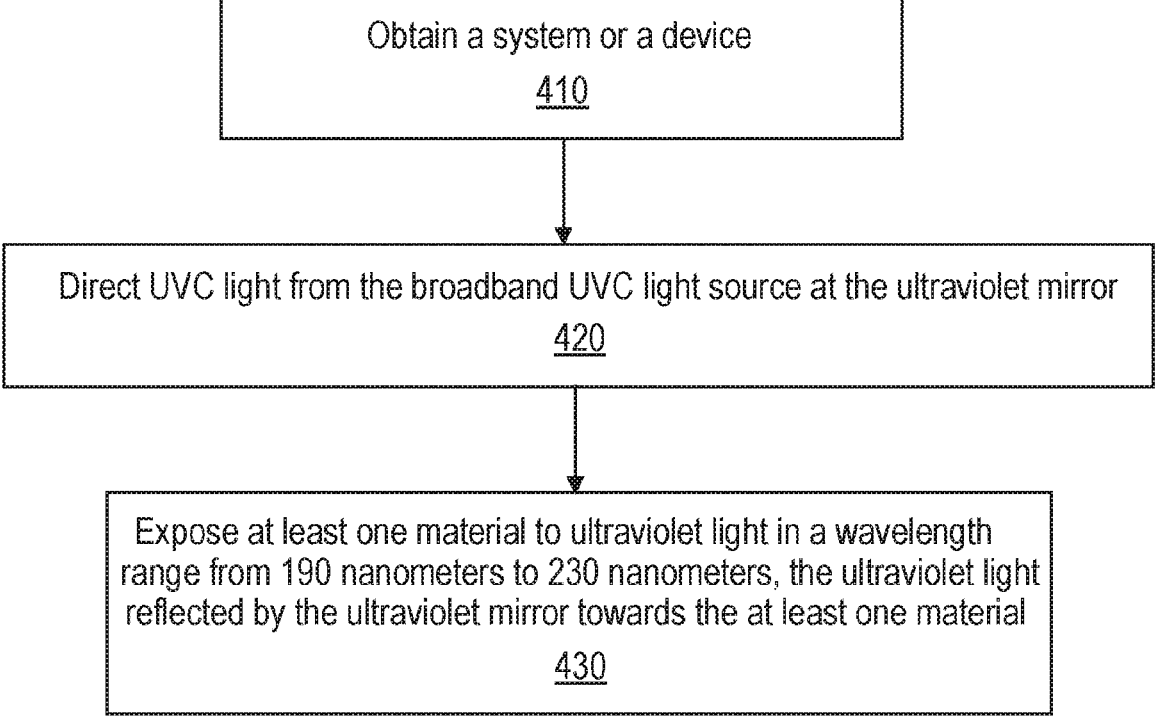
FIG. 4 is a flow chart of an exemplary method according to the present disclosure.

FIG. 4 provides a flow chart of an exemplary method, including Step 410 to obtain a system or a device; Step 420 to direct UVC light from the broadband UVC light source at the ultraviolet mirror; and Step 430 to expose at least one material to ultraviolet light in a wavelength range from 190 nanometers to 230 nanometers, the ultraviolet light reflected by the ultraviolet mirror towards the at least one material. Generally, the at least one material comprises at least one of a solid, a liquid, or a gas. When the device is used in the method, the at least one material is typically located within the chamber of the device at the time of exposure to UVC light. As discussed above, in some cases, it is preferable to expose the material(s) to ultraviolet light having wavelengths of 190 nm or greater, 195 nm, or 200 nm or greater, to 230 nm, 235 nm, or 240 nm.

In preferred embodiments, during the method the one or more materials is exposed to 10, 8, 6, 5, 4, 3, 2, or 1 percent or less of ultraviolet light having a wavelength of greater than 230 nanometers, 235 nm, or 240 nm, to 400 nanometers that is emitted by the broadband UVC source. This is accomplished by effective absorption of those wavelengths by the absorbent layer and/or a chamber, such that 90 percent or more of ultraviolet light having a wavelength of greater than 230 nanometers, 235 nm, or 240 nm, to 400 nanometers is absorbed instead of directed at and/or reflected towards the material(s) during the method.

EXEMPLARY EMBODIMENTS

In a first embodiment, the present disclosure provides a multilayer article. The multilayer article comprises a) an absorbent layer that absorbs at least 50, 60, 70, 80, 90, or 95 percent of incident ultraviolet light having a wavelength between at least 230 nanometers and 400 nanometers, the absorbent layer comprising a major surface; and b) an ultraviolet mirror adjacent to the major surface of the absorbent layer. The ultraviolet mirror is comprised of at least a plurality of alternating first and second optical layers collectively reflecting at an incident light angle of at least one of 0°, 15°, 30°, 45°, 60°, or 75° at least 50, 60, 70, 80, 90, or 95 percent of incident ultraviolet light in a wavelength range from 190 nanometers, 195 nm, or 200 nm, to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers.

In a second embodiment, the present disclosure provides a multilayer article according to the first embodiment, wherein the absorbent layer comprises a silicone thermoplastic, a fluoropolymer, copolymers thereof, or blends thereof.

In a third embodiment, the present disclosure provides a multilayer article according to the first embodiment or the second embodiment, wherein the absorbent layer comprises a fluoropolymer (co)polymer comprising polymerized units derived from one or more monomers selected from tetrafluoroethylene, hexafluoropropylene, vinylidene fluoride, a perfluoroalkoxy alkane, or a combination thereof.

In a fourth embodiment, the present disclosure provides a multilayer article according to any of the first through third embodiments, wherein the absorbent layer further comprises one or more of an ultraviolet radiation absorber, an ultraviolet radiation scatterer, a hindered amine light stabilizer, an anti-oxidant, a pigment, or a combination thereof.

In a fifth embodiment, the present disclosure provides a multilayer article according to the fourth embodiment, wherein the ultraviolet radiation absorber comprises at least one of carbon black, titanium dioxide, zinc oxide, cesium dioxide, or zirconium dioxide.

In a sixth embodiment, the present disclosure provides a multilayer article according to the fourth embodiment or the fifth embodiment, wherein the ultraviolet radiation absorber comprises a benzotriazole compound, a benzophenone compound, a triazine compound, or a combination thereof.

In a seventh embodiment, the present disclosure provides a multilayer article according to any of the first through sixth embodiments, wherein the absorbent layer comprises a continuous metal coating or layer.

In an eighth embodiment, the present disclosure provides a multilayer article according to any of the first through sixth embodiments, wherein the absorbent layer comprises metal particles disposed in a polymer matrix.

In a ninth embodiment, the present disclosure provides a multilayer article according to the seventh embodiment or the eighth embodiment, wherein the metal is selected from silver, gold, copper, nickel, and titanium.

In a tenth embodiment, the present disclosure provides a multilayer article according to any of the first through ninth embodiments, wherein the absorbent layer absorbs at least 30 percent, at least 40 percent, at least 50 percent, at least 60 percent, at least 70 percent, at least 80 percent, or at least 90 percent of incident visible light having a wavelength between at least 400 nanometers and 700 nanometers.

In an eleventh embodiment, the present disclosure provides a multilayer article according to any of the first through tenth embodiments, wherein the at least first optical layer comprises at least one of zirconium oxynitride, hafnia, alumina, magnesium oxide, yttrium oxide, lanthanum fluoride, or neodymium fluoride and wherein the second optical layer comprises at least one of silica, aluminum fluoride, magnesium fluoride, calcium fluoride, silica alumina oxide, or alumina doped silica.

In a twelfth embodiment, the present disclosure provides a multilayer article according to any of the first through tenth embodiments, wherein the at least first optical layer comprises at least one of polyvinylidene fluoride or polyethylene tetrafluoroethylene and wherein the second optical layer comprises fluorinated ethylene propylene (FEP) or a copolymer of tetrafluoroethylene, hexafluoropropylene, and vinylidene fluoride.

In a thirteenth embodiment, the present disclosure provides a multilayer article according to any of the first through twelfth embodiments, wherein the ultraviolet mirror absorbs at an incident light angle of at least one of 0°, 15°, 30°, 45°, 60°, or 75°, at least 30 percent, at least 80 percent, at least 90 percent, at least 95 percent, or at least 98 percent of incident visible light having a wavelength between at least 400 nanometers and 700 nanometers.

In a fourteenth embodiment, the present disclosure provides a multilayer article according to the thirteenth embodiments, wherein the ultraviolet mirror comprises a pigment or a dye.

In a fifteenth embodiment, the present disclosure provides a multilayer article according to any of the first through fourteenth embodiments, wherein the ultraviolet mirror reflects at an incident light angle of at least one of 0°, 15°, 30°, 45°, 60°, or 75°, at least 80 percent, at least 90 percent, at least 95 percent, or at least 98 percent of incident ultraviolet light in a wavelength range from 190 nanometers, 195 nm, or 200 nm, to 230 nanometers, 235 nm, or 240 nm, preferably from 190 nm to 230 nm, from 200 nm to 240 nm, or from 200 nm to 230 nm.

In a sixteenth embodiment, the present disclosure provides a multilayer article according to any of the first through fifteenth embodiments, further comprising an adhesive layer adjacent to the absorbent layer, wherein the absorbent layer is disposed between the ultraviolet mirror and the adhesive layer.

In a seventeenth embodiment, the present disclosure provides a multilayer article according to any of the first through sixteenth embodiments, wherein the ultraviolet mirror is directly attached to the absorbent layer.

In an eighteenth embodiment, the present disclosure provides a multilayer article according to any of the first through sixteenth embodiments, wherein the ultraviolet mirror is separated from the absorbent layer by an air gap.

In a nineteenth embodiment, the present disclosure provides a multilayer article according to any of the first through eighteenth embodiments, further comprising at least one of a heat transfer layer, a plurality of heat transfer fins, or a plurality of heat transfer pins, adjacent to a major surface of the absorbing layer opposite the ultraviolet mirror.

In a twentieth embodiment, the present disclosure provides a multilayer article according to any of the first through nineteenth embodiments, comprising a hollow nonplanar shape.

In a twenty-first embodiment, the present disclosure provides a multilayer article according to any of the first through twentieth embodiments, wherein a major surface of the ultraviolet mirror comprises a plurality of nonplanar features protruding from the major surface.

In a twenty-second embodiment, the present disclosure provides a system. The system comprises a) a broadband UVC light source; and b) the multilayer article according to any of the first through twenty-first or thirty-sixth embodiments.

In a twenty-third embodiment, the present disclosure provides a system according to the twenty-second embodiment, wherein the broadband UVC light source is a low pressure mercury lamp, a medium pressure mercury lamp, a deuterium arc lamp, a xenon arc lamp, or an excimer lamp.

In a twenty-fourth embodiment, the present disclosure provides a system according to the twenty-second embodiment of the twenty-third embodiment, wherein the broadband UVC light source is configured to direct light at the ultraviolet mirror of the multilayer article.

In twenty-fifth embodiment, the present disclosure provides a device. The device comprises a) a chamber, the chamber comprising at least one wall; b) a broadband UVC light source located within the chamber; c) an absorbent layer adjacent to the at least one wall of the chamber; and d) an ultraviolet mirror located within the chamber between the broadband UVC light source and the absorbent layer. The ultraviolet mirror is comprised of at least a plurality of alternating first and second optical layers collectively reflecting at an incident light angle of at least one of 0°, 15°, 30°, 45°, 60°, or 75°, at least 50, 60, 70, 80, 90, or 95 percent of incident ultraviolet light in a wavelength range from 190 nanometers, 195 nm, or 200 nm, to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers. At least 50, 60, 70, 80, 90, or 95 percent of ultraviolet light having a wavelength between at least 230 nanometers and 400 nanometers transmitted through the ultraviolet mirror is absorbed in the chamber.

In twenty-sixth embodiment, the present disclosure provides a device according to the twenty-fifth embodiment, wherein the absorbent layer absorbs at least 10, 20, 30, 40, 50, 60, 70, 80, 90, or 95 percent of incident ultraviolet light having a wavelength between at least 230 nanometers and 400 nanometers.

In twenty-seventh embodiment, the present disclosure provides a device according to the twenty-fifth embodiment or the twenty-sixth embodiment, wherein the broadband UVC light source is configured to direct light at the ultraviolet mirror.

In twenty-eighth embodiment, the present disclosure provides a device according to any of the twenty-fifth through twenty-seventh embodiments, wherein the ultraviolet mirror and the absorbent layer are separate from each other.

In twenty-ninth embodiment, the present disclosure provides a device according to any of the twenty-fifth through twenty-eighth embodiments, wherein the absorbent layer is directly adjacent to the at least one wall of the chamber.

In a thirtieth embodiment, the present disclosure provides a method of disinfecting at least one material. The method comprises a) obtaining a system according to any of the twenty-second through twenty-fourth embodiments or a device according to any of the twenty-fifth through twenty-ninth embodiments; b) directing UVC light from the broadband UVC light source at the ultraviolet mirror; and c) exposing the at least one material to ultraviolet light in a wavelength range from 190 nanometers to 240 nanometers, the ultraviolet light reflected by the ultraviolet mirror towards the at least one material.

In a thirty-first embodiment, the present disclosure provides a method according to the thirtieth embodiment, wherein the at least one material comprises at least one of a solid, a liquid, or a gas.

In a thirty-second embodiment, the present disclosure provides a method according to the thirtieth embodiment or the thirty-first embodiment, wherein the at least one material is located within the chamber of the device.

In a thirty-third embodiment, the present disclosure provides a method according to any of the thirtieth through thirty-second embodiments, wherein step c) is performed until achievement of a log 2, log 3, log 4, or greater reduction of at least one microorganism on or in the at least one material, as compared to an amount of the at least one microorganism present prior to step c).

In a thirty-fourth embodiment, the present disclosure provides a method according to any of the thirtieth through thirty-third embodiments, wherein the at least one material is exposed to 10, 8, 6, 5, 4, 3, 2, or 1 percent or less of ultraviolet light having a wavelength between greater than 230 nanometers and 400 nanometers that is emitted by the broadband UVC source.

In a thirty-fifth embodiment, the present disclosure provides a system. The system comprises a UVC collimator, a broadband UVC light source, and a multilayer article comprising a UVC mirror and an absorbent layer. The multilayer article is disposed adjacent to a ceiling of a room and the UVC collimator is configured to collimate light from the broadband UVC light source and direct the collimated light at an angle towards the UVC mirror of the multilayer article adjacent to the ceiling. The absorbent layer absorbs at least 50, 60, 70, 80, 90, or 95 percent of incident ultraviolet light having a wavelength between at least 230 nanometers and 400 nanometers. The absorbent layer comprises a major surface and the ultraviolet mirror is adjacent to the major surface of the absorbent layer. The ultraviolet mirror is comprised of at least a plurality of alternating first and second optical layers collectively reflecting at least 50, 60, 70, 80, 90, or 95 percent of incident ultraviolet light in a wavelength range from 200 nm to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers.

In a thirty-sixth embodiment, the present disclosure provides a multilayer article according to any of the first through ninth or eleventh through twenty-first embodiments, wherein the absorbent layer reflects at least 30 percent, at least 40 percent, at least 50 percent, at least 60 percent, at least 70 percent, at least 80 percent, or at least 90 percent of incident visible light having a wavelength between at least 400 nanometers and 700 nanometers.

Advantages and embodiments of this invention are further illustrated by the following examples, but the particular materials and amounts thereof recited in these examples, as well as other conditions and details, should not be construed to unduly limit this invention. All parts and percentages are by weight unless otherwise indicated.

EXAMPLES

Example 1

A UVC mirror reflecting wavelengths over the range of 200 nm to 240 nm was made by vapor coating an inorganic optical stack having first optical layers comprising $HfO_2$ and second optical layers comprising $SiO_2$ onto a 100 micrometers (4 mil) thick fluoropolymer film (obtained under the trade designation "NOWOFLON THV 815" from Nowofol Kunststoffprodukte GmbH & Co. KG, Siegsdorf, Germany). More specifically, a thin film stack comprised of alternating layers of $HfO_2$ and $SiO_2$ and designed to have peak reflectance at 200 nm, began by coating layer 1 $HfO_2$ at 23.5 nm. In electron beam deposition, a four-hearth evaporation source was used. Each hearth was cone-shaped and 17 $cm^3$ volume of $HfO_2$ chunks filled it. A magnetically deflected high voltage electron beam was raster scanned over the material surface as filament current of the beam was steadily, in a pre-programmed fashion, increased. Upon completion of the pre-programmed step, the $HfO_2$ surface was heated to evaporation temperature, about 2500° C., and a source shutter opened, the $HfO_2$ vapor flux emerged from the source in a cosine-shaped distribution and condensed upon the substrate material above the source. For enhancement of coating uniformity, the substrate holders rotated during deposition. Upon reaching the prescribed coating thickness (23.5 nm) the filament current was shut off, the shutter closed and the $HfO_2$ material cooled. For layer 2 the evaporation source was then rotated to a hearth containing chunks of $SiO_2$ and a similar pre-programmed heating process began. Here, the $SiO_2$ surface temperature was about 950° C. when the source shutter opened and, upon reaching the prescribed coating thickness (34.2 nm), the filament current was shut off, the shutter closed and the $SiO_2$ material cooled. This stepwise process was continued, layer by layer, until a total number of 11 layers was reached. Reflectance was measured with a spectrophotometer (obtained under the trade designation "LAMBDA 1050 UV-VIS" from Perkin-Elmer, Waltham, MA) and found to be 97.9% at 222 nm and 18.2% at 254 nm.

A UV absorbent film was made by extrusion compounding 30 wt. % $TiO_2$ (obtained from Americhem Co., Cuyahoga Falls, OH) with a fluoropolymer (obtained under the trade designation "3M DYNEON THV 500GZ" from 3M, St. Paul, MN) and casting into a 200 micron thick film on a chilled roll at 24 ft/min (7.32 m/min).

Figure 5:
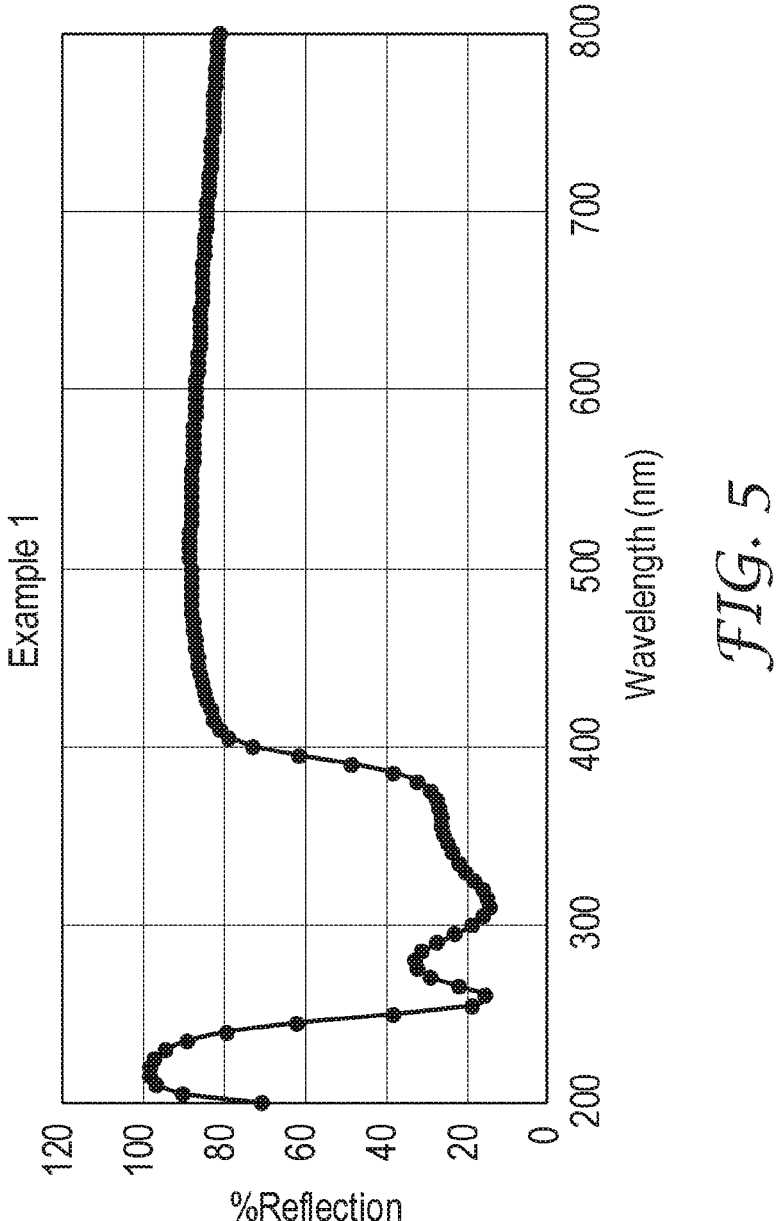
FIG. 5 is a graph of reflection spectra of an ultraviolet mirror prepared in Example 1.

The UVC mirror film was then heat laminated to the UV absorbent fluoropolymer film in an oven at 130° C. under 5 lbs (2.27 kg) of weight for 2 hrs. This heat laminated UV mirror film stack was measured with a spectrophotometer (LAMBDA 1050 UV-VIS) to have an average % reflection of 89.9% over the wavelength range of 200 nm to 240 nm, as shown in FIG. 5.

Example 2—Prophetic

A UVC mirror film reflecting over the range 200 nm to 240 nm could be created by sputter coating an inorganic optical stack having first optical layers comprising $ZrO_xN_y$ and second optical layers comprising $SiAl_xO_y$ onto 100 microns thick fluoropolymer film (available under the trade designation "NOWOFLON THV 815" from Nowofol Kunststoffprodukte GmbH & Co. KG, Siegsdorf, Germany).

A UVC mirror film can be coated in continuous roll to roll (R2R) fashion, using $ZrO_xN_y$ as the high refractive index material and $SiAl_xO_y$ as the low refractive index material. The optical design is alternating quarter wave thickness layers of the two materials tuned to start reflecting at 200 nm with a gradient of layer thickness resulting in the last layers of the stack reflecting at 240 nm. For $ZrO_xN_y$, with refractive index of 3.1 at 200 nm, the physical thickness target is 17.74 nm. For $SiAl_xO_y$, here sputtered from an aluminum-doped silicon sputter target, with refractive index 1.57, the target thickness is 35 nm. Layer one $ZrO_xN_y$ is DC sputtered from a pure zirconium sputter target in a gas mixture of argon, oxygen and nitrogen. Whereas argon is the primary sputtering gas, oxygen and nitrogen levels are set to achieve transparency, low absorptance and high refractive index. The film roll transport initially starts at a pre-determined speed, and the sputter source power is ramped to full operating power, followed by introduction of the reactive gases and then achieving steady state condition. The sputter source is orthogonal to and wider than the film which is being coated. Upon reaching the desired length of coated film the reactive gases are set to zero and the target is sputtered to provide a pure Zr surface state. The film direction is next reversed and silicon (aluminum doped) is deposited using a rotary pair of sputter targets using AC frequency (40 kHz) power applied in an argon sputtering atmosphere. Upon reaching steady state, oxygen reactive gas is introduced to provide transparency and low refractive index. At the pre-determined process setting and line speed the second layer is coated over the length which was coated for the first layer. The sputter sources are orthogonal to and wider than the film being coated. After reaching the desired length of coated film the reactive oxygen is removed and the target is sputtered in argon to provide a pure silicon (aluminum doped) surface state. This stepwise process is continued, layer by layer, until a total number of 9 layers is reached. Resulting peak reflectance is expected to be 95% at 222 nm with a decrease to a lower reflectance of 20% at 254 nm when measured with a spectrophotometer ("LAMBDA 1050 UV-VIS"). A UV absorbent film can be made by extrusion compounding 30 wt. % $TiO_2$ (available from Americhem, Cuyahoga Falls, OH) with fluoropolymer "3M DYNEON THV 500GZ" and casting into a 200 micron thick film onto a chilled roll at 10 ft/min (3.05 m/min). The UVC mirror film can then be laminated to the UV absorbent fluoropolymer film in an oven at 130° C. under 5 lbs (2.27 kg) of weight for 2 hrs. This heat laminated UV mirror film stack would be measured with a spectrophotometer ("LAMBDA 1050 UV-VIS") and expected to have an average % reflection of 89.9% over the wavelength range of 200 nm to 240 nm.

Example 3

Figure 6:
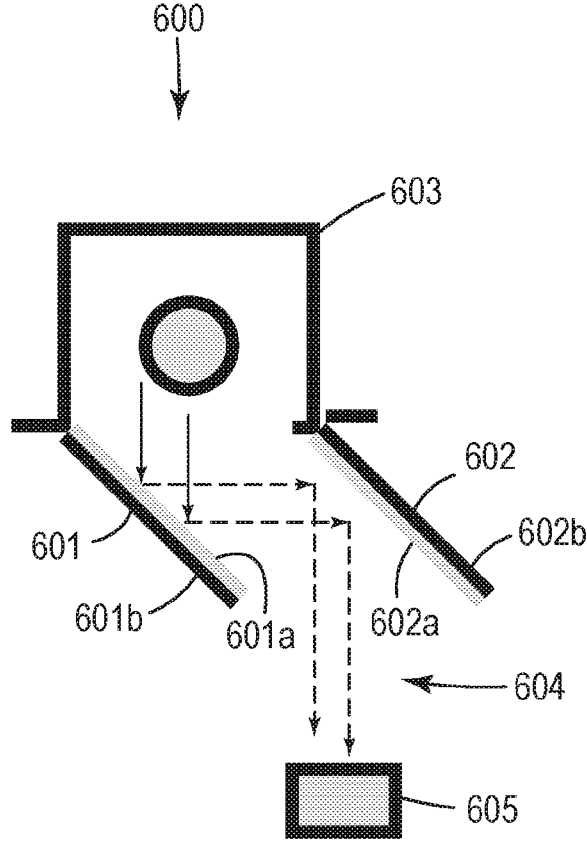
FIG. 6 is a schematic cross-sectional view of an exemplary system prepared according to the present disclosure.

Referring to FIG. 6, a UVC disinfection system 600 was prepared including a multilayer article 601 and a UVC light source 603 (MICROBEBUSTER available from Sterilray, Somersworth, NH), according to the present disclosure. The multilayer article 601 included a UVC mirror film 601a made as described in Example 1, but instead of using the $TiO_2$ filled THV500 UVC absorbing layer, a 125 micron thick layer of UVC absorbing polyester film 601b available from DuPont Teijin Films U.S. Limited Partnership, Chester, VA under the trade name MELINEX ST505 was used in the multilayer article 601. The UVC mirror film 601a having a reflection band of 200-240 nm was attached to the polyester film 601b substrate, which absorbs UVC in the range of 200-320 nm. The multilayer article 601 was positioned at a 45 degree angle with respect to an aperture through which light is emitted from the UVC light source 603 (positioned so UVC light was directed at the UVC mirror film 601*a*) to reflect UVC wavelengths of 200-240 nm emitted by the UVC light source 603 onto an opposing second multilayer article 602 positioned spaced apart from and parallel to the first multilayer article 601. The second multilayer article 602 included a UVC mirror film 602*a* also having a reflection band of 200-240 nm attached to a polyester film 602*b* substrate which absorbs UVC in the range of 200-320 nm, prepared the same way as the first multilayer film 601 and positioned so UVC light reflected off the first multilayer article 601 was directed at the UVC mirror film 602*a*. The multilayer articles 601, 602 were each 24 inches (60.96 centimeters) long in the direction of the UVC source 603 bulb length and 12 inches (30.48 centimeters) wide. The second UVC Mirror film 602 reflects 222 nm UVC light 604 downward with less 254 nm UVC being reflected downward. The ratio of 222 nm to 254 nm UVC intensity measured with a UVC light sensor 605 located 76 cm below the UVC light source 603 after reflection off the two multilayer articles 601, 602, was 30.9. The ratio of 222 nm to 254 nm UVC intensity measured 76 cm below the UVC light source 603 when lacking the two multilayer articles 601, 602, was 15.8. The double reflection of UVC light from the UVC mirror films (having 200-320 nm UVC absorption behind each UVC mirror film) increased the 222 nm to 254 nm UVC intensity ratio by 95%.

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A multilayer article comprising:
   a) an absorbent layer that absorbs at least 50, 60, 70, 80, 90, or 95 percent of incident ultraviolet light having a wavelength between at least 230 nanometers and 400 nanometers while absorbing at least 70 percent of incident visible light having a wavelength between at least 400 nm and 700 nm, the absorbent layer comprising a major surface; and
   b) an ultraviolet mirror adjacent to the major surface of the absorbent layer, wherein the ultraviolet mirror is comprised of at least a plurality of alternating first and second optical layers collectively reflecting at an incident light angle of at least one of 0°, 15°, 30°, 45°, 60°, or 75°, at least 50, 60, 70, 80, 90, or 95 percent of incident ultraviolet light in a wavelength range from 190 nanometers, 195 nm, or 200 nm, to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers.

2. The multilayer article of claim 1, wherein the absorbent layer comprises a silicone thermoplastic, a fluoropolymer, copolymers thereof, or blends thereof.

3. The multilayer article of claim 1, wherein the absorbent layer further comprises one or more of an ultraviolet radiation absorber, an ultraviolet radiation scatterer, a hindered amine light stabilizer, an anti-oxidant, a pigment, or a combination thereof.

4. The multilayer article of claim 1, wherein the absorbent layer comprises a continuous metal coating or layer.

5. The multilayer article of claim 1, wherein the absorbent layer comprises metal particles disposed in a polymer matrix.

6. The multilayer article of claim 1, wherein the absorbent layer absorbs at least 90 percent of incident visible light having a wavelength between at least 400 nanometers and 700 nanometers.

7. The multilayer article of claim 1, wherein the at least first optical layer comprises at least one of zirconium oxynitride, hafnia, alumina, magnesium oxide, yttrium oxide, lanthanum fluoride, or neodymium fluoride and wherein the second optical layer comprises at least one of silica, aluminum fluoride, magnesium fluoride, calcium fluoride, silica alumina oxide, or alumina doped silica.

8. The multilayer article of claim 1, wherein the at least first optical layer comprises at least one of polyvinylidene fluoride or polyethylene tetrafluoroethylene and wherein the second optical layer comprises fluorinated ethylene propylene (FEP) or a copolymer of tetrafluoroethylene, hexafluoropropylene, and vinylidene fluoride.

9. The multilayer article of claim 1, wherein the ultraviolet mirror is separated from the absorbent layer by an air gap.

10. The multilayer article of claim 1, further comprising at least one of a heat transfer layer, a plurality of heat transfer fins, or a plurality of heat transfer pins, adjacent to a major surface of the absorbing layer opposite the ultraviolet mirror.

11. The multilayer article of claim 1, comprising a hollow nonplanar shape.

12. The multilayer article of claim 1, wherein a major surface of the ultraviolet mirror comprises a plurality of nonplanar features protruding from the major surface.

13. A system comprising:
   a) a broadband UVC light source; and
   b) the multilayer article of claim 1.

14. The system of claim 13, wherein the broadband UVC light source is a low pressure mercury lamp, a medium pressure mercury lamp, a deuterium arc lamp, a xenon arc lamp, or an excimer lamp.

15. The system of claim 13, wherein the broadband UVC light source is configured to direct light at the ultraviolet mirror of the multilayer article.

16. A method of disinfecting at least one material, the method comprising:
   a) obtaining a system of claim 13;
   b) directing UVC light from the broadband UVC light source at the ultraviolet mirror; and
   c) exposing the at least one material to ultraviolet light in a wavelength range from 190 nanometers, 195 nm, or 200 nm, to 230 nanometers, 235 nm, or 240 nm, the ultraviolet light reflected by the ultraviolet mirror towards the at least one material.

17. A device comprising:
   a) a chamber, the chamber comprising at least one wall;
   b) a broadband UVC light source located within the chamber;
   c) an absorbent layer adjacent to the at least one wall of the chamber that absorbs at least 70 percent of incident visible light having a wavelength between at least 400 nm and 700 nm; and
   d) an ultraviolet mirror located within the chamber between the broadband UVC light source and the absorbent layer, wherein the ultraviolet mirror is comprised of at least a plurality of alternating first and second optical layers collectively reflecting at an incident light angle of at least one of 0°, 15°, 30°, 45°, 60°, or 75°, at least 50, 60, 70, 80, 90, or 95 percent of incident ultraviolet light in a wavelength range from 190 nanometers, 195 nm, or 200 nm, to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers, wherein at least 50, 60, 70, 80, 90, or 95 percent of ultraviolet light having a wavelength between at least 230 nanometers and 400 nanometers transmitted through the ultraviolet mirror is absorbed in the chamber.

18. The device of claim 17, wherein the ultraviolet mirror and the absorbent layer are separate from each other.

19. A method of disinfecting at least one material, the method comprising:

a) obtaining a system comprising:

a broadband UVC light source; and a multilayer article comprising:

an absorbent layer that absorbs at least 50, 60, 70, 80, 90, or 95 percent of incident ultraviolet light having a wavelength between at least 230 nanometers and 400 nanometers the absorbent layer comprising a major surface; and an ultraviolet mirror adjacent to the major surface of the absorbent layer, wherein the ultraviolet mirror is comprised of at least a plurality of alternating first and second optical layers collectively reflecting at an incident light angle of at least one of 0°, 15°, 30°, 45°, 60°, or 75°, at least 50, 60, 70, 80, 90, or 95 percent of incident ultraviolet light in a wavelength range from 190 nanometers, 195 nm, or 200 nm, to 230 nanometers, 235 nm, or 240 nm, and collectively transmitting at an incident light angle of at least one of 0°, 15°, 30°, 45°, 60°, or 75°, at least 50, 60, 70, 80, 90, or 95 percent of incident ultraviolet light in a wavelength range from greater than 230 nanometers, greater than 235 nm, or greater than 240 nm, to 400 nanometers;

b) directing UVC light from the broadband UVC light source at the ultraviolet mirror; and c) exposing the at least one material to ultraviolet light in a wavelength range from 190 nanometers, 195 nm, or 200 nm, to 230 nanometers, 235 nm, or 240 nm, the ultraviolet light reflected by the ultraviolet mirror towards the at least one material, wherein the at least one material is exposed to 10, 8, 6, 5, 4, 3, 2, or 1 percent or less of ultraviolet light having a wavelength between greater than 230 nanometers, 235 nm, or 240 nm, and 400 nanometers that is emitted by the broadband UVC source.

\* \* \* \* \*